United States Patent
German et al.

(10) Patent No.: US 6,225,290 B1
(45) Date of Patent: *May 1, 2001

(54) SYSTEMIC GENE THERAPY BY INTESTINAL CELL TRANSFORMATION

(75) Inventors: Michael German, San Francisco; Ira D. Goldfine, Kentfield; Stephen S. Rothman, Berkeley, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/717,084

(22) Filed: Sep. 19, 1996

(51) Int. Cl.$^7$ .............................. A61K 48/00; C12N 15/00

(52) U.S. Cl. ......................... 514/44; 435/320.1; 435/455; 435/458

(58) Field of Search .............................. 514/44; 435/325, 435/320.1, 455, 458; 536/23.1, 23.5, 23.51; 935/52, 55, 54, 66, 70, 76, 77, 78; 424/93.21

(56) References Cited

U.S. PATENT DOCUMENTS

| | | | |
|---|---|---|---|
| 5,292,662 | 3/1994 | Sandmeyer | 435/325 |
| 5,328,470 | * 7/1994 | Nabel et al. | 604/101 |
| 5,643,579 | * 7/1997 | Hung et al. | 424/227.1 |
| 5,681,744 | * 10/1997 | Greenstein | 435/320.1 |
| 5,786,340 | * 7/1998 | Henning et al. | 514/44 |
| 5,821,235 | * 10/1998 | Henning et al. | 514/44 |

FOREIGN PATENT DOCUMENTS

| | | |
|---|---|---|
| WO 90/11092 | 10/1990 | (WO) . |
| WO 93/03769 | 3/1993 | (WO) . |
| WO 93/19660 | 10/1993 | (WO) . |
| WO 94/25608 | 11/1994 | (WO) . |
| WO 96/40081 | 12/1996 | (WO) . |

OTHER PUBLICATIONS

Anderson, Nature, vol. 392, 25–30, Apr. 1998.*
Cryz et al., Vaccine, vol. 14, 7, Vaccine Delivery Systems, Reports of the Expert Panels, pp. 665–688, 1996.*
Wirtz et al. (GUT, 44, 6, pp. 800–807), 1999.*
Doerfler et al. (Gene, 157/1–2, pp. 241–245), 1995.*
Filion et al. (Int. J. Pharm, 162(1–2), pp. 159–170), 1998.*
Tait et al. (Clinical Cancer Res., vol. 5, 1707–1714), 1999.*
Docherty (Clinical Science, 92:321–330, 1997).*
Taniguchi et al.(J. Surgical Res., 70:41–45, 1997).*
Takehara et al. (Human Gene Therapy, 7, 5:589–93, Mar. 1996).*
Batra, Raj K., 1994. "Molecular Conjugate Vectors Mediate Efficient Gene Transfer into Gastrointestinal Epithelial Cells", *Cancer Gene Therapy* 1(3):185–92.
Benvenisty, Nissim, and Reshef, L., 1986. "Direct Introduction of Genes into Rats and Expression of the Genes", *Proc. Natl. Acad. Sci. USA* 83:9551–5.

Chang, A.G.Y. and Wu, G.Y. 1994. "Gene Therapy: Applications to the Treatment of Gastrointestinal and Liver Diseases", *Gastroenterol.* 106:1076–84.
Dubensky, T.W., et al., 1984. "Direct Transfection of Viral and Plasmid DNA into the Liver or Spleen of Mice", *Proc. Natl. Acad. Sci. USA* 81:7529–7533.
German, M.S., and Wang, J., 1994."The Insulin Gene Contains Multiple Transcriptional Elements that Respond to Glucose", *Mol. Cell. Biol.* 14:4067.
Jones, Stephen N., et al., 1990. "Ectopic Correction of Ornithine Transcarbamylase Deficiency in Sparse Fur Mice", *J. Biol. Chem.* 264(24):14684–90.
Lau, C., et al., 1992. "The Intestine as a Possible Site for Gene Therapy", *J. Cell Biochem.* 16F(V215):48.
Ledley, F.D. 1992. "Somatic Gene Therapy in Gastroenterology: Approaches and Applications", *J. Pediatr. Gastroenterol. Nutr.* 14:328–37.
Liebow, C., and Rothman, S.S., 1975. "Enteropancreatic Circulation of Digestive Enzymes", *Science* 189:472–474.
Mazière, J. C., et al., 1992. "Processing and Characterization of the Low Density Lipoprotein Receptor in the Human Colonic Carcinoma Cell Subclone HT29–18: A Potential Pathway for Deliverying Therapeutic Drugs and Genes", *Bioscience Reports*, 12(6):483–94.
Morsey, M.A. et al., 1993. "Progress Toward Human Gene Therapy", *JAMA* 270(19): 2338–2345.
Noel, Adam R., et al., 1994. "Optimization of Gene Transfer into Intestinal Epithelial Cells Using a Retroviral Vector", *J. Ped. Gastroenterol. Nutrition* 19(1):43–9.
Puppi, M. and Henning, S.J., 1995. "Cloning of the Rat Ecotropic Retroviral Receptor and Studies of Its Expression in Intestinal Tissues", *P.S.E.B.M.* 209:38–45.
Rosenfeld, M. A., et al., 1991. "Adenovirus–Mediated Transfer of a Recobinant αl–Antitrypsin Gene to the Lung Epithelium in Vivo", *Science* 252:431–4.

(List continued on next page.)

*Primary Examiner*—John L. LeGuyader
*Assistant Examiner*—Dave Trong Nguyen
(74) *Attorney, Agent, or Firm*—Paula A. Borden; Carol L. Francis; Bozicevic, Field & Francis LLP

(57) ABSTRACT

Intestinal epithelial cells of a mammalian subject are genetically altered to operatively incorporate a gene which expresses a protein which has a desired therapeutic effect. Intestinal cell transformation is accomplished by administration of a formulation composed primarily of naked DNA, and is preferably administered orally. Oral or other intragastrointestinal routes of administration provide a simple method of administration, while the use of naked nucleic acid avoids the complications associated with use of viral vectors to accomplish gene therapy. The expressed protein is secreted directly into the gastrointestinal tract and/or blood stream to obtain therapeutic blood levels of the protein thereby treating the patient in need of the protein. The transformed intestinal epithelial cells provide short or long term therapeutic cures for diseases associated with a deficiency in a particular protein or which are amenable to treatment by overexpression of a protein.

14 Claims, 9 Drawing Sheets

OTHER PUBLICATIONS

Sandberg, J.W., et al. 1994. "Improving Access to Intestinal Stem Cells as a Step Toward Intestinal Gene Transfer", *Hum. Gene Therap.* 5:303–9.

Soriano–Bucher, H. et al. 1991. "Gene Transfer into the Intestinal Epithelium", *Gastroenterol.* 100(5): A252.

Sweetser, D. A., et al., 1988. "Transgenic Mice Containing Intestinal Fatty Acid–Binding Protein–Human Growth Hormone Fusion Genes Exhibit Correct Regional and Cell–Specific Expression of the Reporter Gene in their Small Intestine", *Proc. Natl. Acad. Sci. USA* 85:9611–5.

Traber, P.G. et al., 1992. "Novel DNA–Binding Proteins Regulate Intestine–Specific transcription of the Sucrase–Isomaltase Gene". *Mol. Cell. Biol.* 12(8):3614–27.

Coghlan, New Scientist, Nov. 1995, p. 14–15, vol. 148.*

Ledley, Hum. Gene Ther., 6, 1129–1144, 1995.*

Mastrangelo et al., Seminars in Oncology, vol. 23, pp. 4–21, 1996.*

* cited by examiner

SYSTEMIC GENE THERAPY BY INTESTINAL CELL TRANSFORMATION

FIELD OF THE INVENTION

This invention relates generally to the field of gene therapy and more particularly to the application of gene therapy to the cells of the intestine.

BACKGROUND OF THE INVENTION

Gene therapy has attracted wide attention as a method to treat various mammalian diseases and enhance production of specific proteins or other cellular products. Gene therapy is generally accomplished by introducing exogenous genetic material into a mammalian patient's cells. The introduced genetic material can be designed to replace an abnormal (defective) gene of the mammalian patient ("gene replacement therapy"), or can be designed for expression of the encoded protein or other therapeutic product without replacement of any defective gene ("gene augmentation"). Because many congenital and acquired medical disorders result from inadequate production of various gene products, gene therapy provides a means to treat these diseases through either transient or stable expression of exogenous nucleic acid encoding the therapeutic product.

Gene therapy can be accomplished by either direct transformation of target cells within the mammalian subject (in vivo gene therapy) or transformation of cells in vitro and subsequent implantation of the transformed cells into the mammalian subject (ex vivo gene therapy). In vivo gene therapy has been an area of particular interest, especially in transformation of somatic cells to repair particular defects in these cells, such as the administration of gene vectors to the upper respiratory tract in cystic fibrosis.

In addition to repair of somatic cells, in vivo gene therapy can also be used for systemic treatment, an area in which gene therapy has broad applications. Systemic treatment involves transfecting target cells with the DNA of interest, expressing the coded protein in that cell, and the capability of the transformed cell to subsequently secrete the manufactured protein into blood.

A variety of methods have been developed to accomplish in vivo transformation including mechanical means (e.g, direct injection of nucleic acid into target cells or particle bombardment), recombinant viruses, liposomes, and receptor-mediated endocytosis (RME) (for reviews, see Chang et al. 1994 *Gastroenterol.* 106:1076–84; Morsy et al. 1993 *JAMA* 270:2338–45; and Ledley 1992 *J. Pediatr. Gastroenterol. Nutr.* 14:328–37).

As with all therapies, the therapy that is most easily administered, least expensive, and most likely to realize patient compliance is the therapy of choice. Intestinal gene therapy provides such a therapy in the realm of gene therapy techniques. The intestinal epithelium is a particularly attractive site for in vivo gene therapy, largely due to the ease of access via an oral or other lumenal route. Administration of the exogenous nucleic acid to achieve in vivo transformation can be accomplished by non-invasive procedures. For example, the patient can simply take a pill composed of the exogenous nucleic acid or alternatively the exogenous nucleic acid formulation can be administered by some other non-invasive means (i.e., a means that does not require a major surgical procedure, such as endoscopic catheterization or rectal suppository incision).

Methods for accomplishing in vivo intestinal gene therapy have met with severe obstacles. Because the field has been primarily concerned with long-term gene therapy, most groups have shunned intestinal epithelial cells as targets for in vivo gene therapy due to the cells' rapid turn-over rate (2 to 4 days) (see, e.g., Sandberg et al. 1994 *Hum. Gene Therap.* 5:303–9). Efforts to achieve in vivo transformation may be further complicated by the mucus layer of the intestine, which is thought to block access of the gene therapy transforming formulation to the target cells (Sandberg et al., supra). The presence of high concentrations of DNAses in the intestinal tract is also thought to be a formidable barrier to the effective introduction of DNA into intestinal tract cells.

Many of the vectors and delivery systems developed for in vivo gene therapy either have their own inherent drawbacks or are not entirely suitable for in vivo intestinal gene therapy. For example, recombinant viruses, particularly retroviruses, may be slow in gaining FDA approval due to concerns generally associated with the administration of live viruses to humans. In addition, it has become clear that viral vectors present problems with the possibility of multiple administrations of the gene construct due to immune responses, and may greatly limit their utility. Mechanical means, such as the gene gun, are designed for use in transformation of skeletal muscle cells and are not particularly useful in intestinal cell transformation due to problems of access and to the delicate nature of organ.

Current methods of gene therapy designed to accomplish systemic therapeutic goals are limited to ex vivo techniques that require complex procedures to transform cells, pose the potential of rejection of the transplant, require at least minor invasive procedures, and limit implantation to modest numbers of cells. In vivo methods can also be used for systemic therapy, but these frequently require invasive procedures. Thus, there is a need in the field for a method to accomplish in vivo transformation of intestinal epithelial cells. The present invention addresses these problems by providing a non-invasive gene therapy method that uses naked nucleic acid constructs either alone or in combination with various adjuvants.

SUMMARY OF THE INVENTION

Intestinal epithelial cells are genetically altered by exposure to a formulation primarily composed of naked nucleic acid sequences, including DNA, RNA, DNA-RNA hybrids, oligonucleotides, and synthetic nucleic acids to operatively incorporate a gene which expresses a therapeutically effective protein. More particularly, cells of the intestine are genetically altered to operatively incorporate a functional exogenous DNA sequence which when expressed produces a protein which has a desired therapeutic effect on the patient. The expressed protein is secreted directly from the cell into the blood stream and/or into the gastrointestinal system in an amount sufficient to obtain therapeutic levels of the protein, thereby treating the patient in need of the protein. The method of the invention can thus be used to accomplish gene therapy in which somatic cells are transformed to achieve systemic therapy and/or repair of defects in the transfected cell itself.

A primary object is to provide a method of gene therapy wherein cells of the intestinal epithelium, (e.g., cells of the small intestine or the large intestine) of a mammal are genetically modified by the incorporation of fully functional genes (exogenous DNA) which express a biologically active and therapeutically useful protein which protein is secreted from the modified cells into the circulatory system, the gastrointestinal tract, and/or the local environment of gastrointestinal tissue.

Another object is to produce genetically transformed intestinal epithelial cells which have incorporated into their genome exogenous genetic material in the form of a fully functional gene which expresses a biologically active and therapeutically useful protein that functions within the cell. Alternatively, the transfected nucleic acid can provide structural, enzymatic or other direct intracellular effects independent of coding for a gene product. Examples include anti-sense nucleic acids that effect the regulation and expression of endogenous genes, and ribozymes which are nucleic acid sequences having intrinsic enzymatic activity.

One advantage of the present invention is that either short term or long term cures and/or treatment of disease symptoms can be provided for individuals suffering from a disease due to a deficiency in a particular protein.

Another advantage of the present invention is that the short term expression of the therapeutic gene in the individual allows for regulation of administration of the therapeutic gene product to the patient. Because intestinal cells turn over rapidly, expression can be easily modified or altered by varying the dose and/or formulation of the oral preparation.

Another advantage of the invention is that the method completely avoids invasive procedures, and allows the vector to be administered in the simplest possible fashion—by the oral administration of a pill or other material.

Another advantage of the invention is that naked DNA is used as the vector, rather than viral vectors. Although viral vectors have been popular for gene therapy due to ease of administration and the incorporation of DNA into the genome, viral vectors have been found to produce substantial antigenic reactions that prevent their multiple administration. Use of naked DNA avoids this problem.

Yet another advantage of the invention is that potential deleterious side-effects of long term gene administration can be avoided, because the epithelial cells are sloughed into the intestinal lumen and lost from the body within a few days.

A feature of the present invention is that the expressed protein is secreted into the circulatory system or into the gastrointestinal tract to provide a systemic effect.

These and other objects, advantages and features of the present invention will become apparent to those persons skilled in the art upon reading the details of the vectors, formulations, and methodology as more fully set forth below.

DESCRIPTION OF THE PREFERRED EMBODIMENTS

Figure 1:
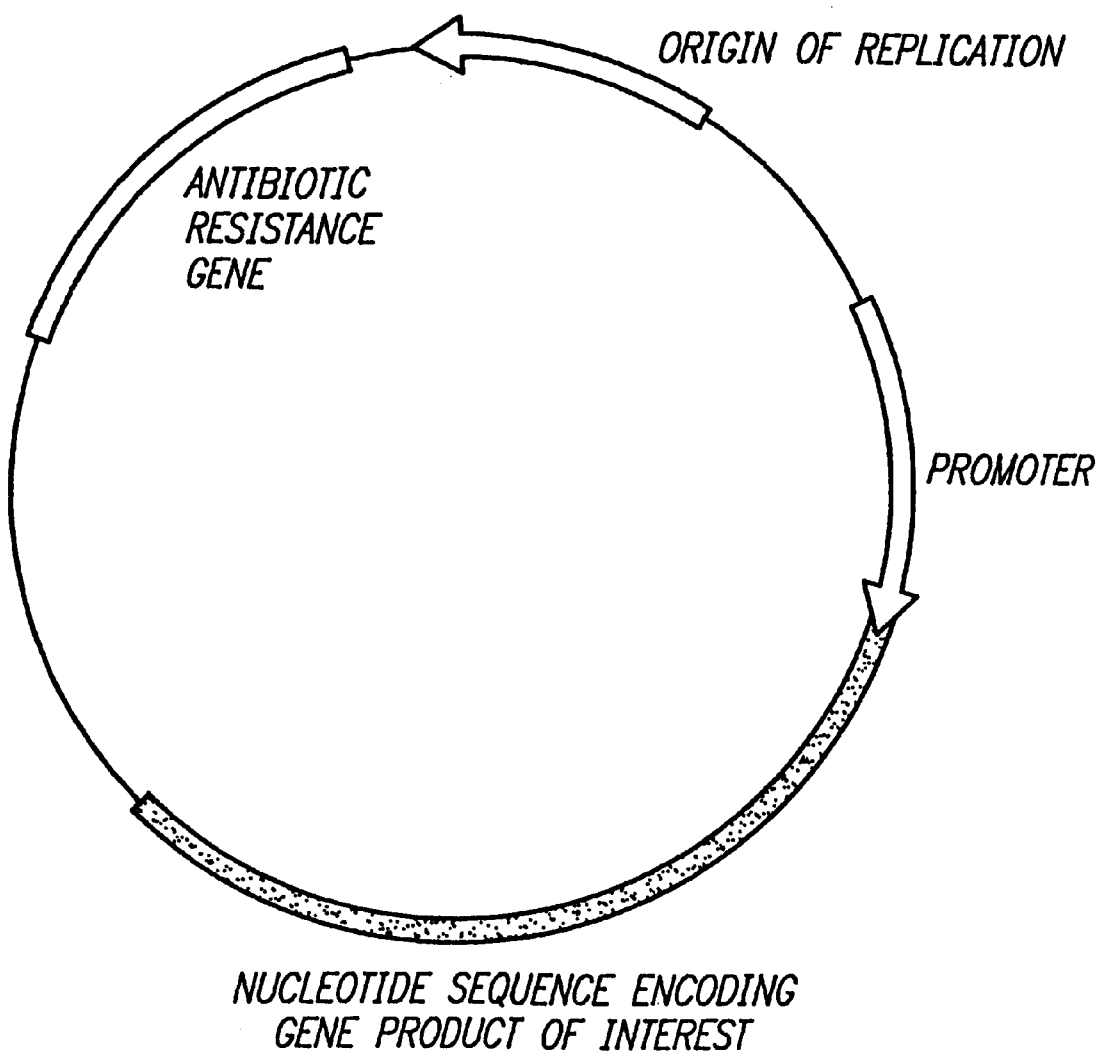
FIG. 1 is a schematic view of an exemplary recombinant plasmid construct useful in transformation of intestinal epithelial cells according to the invention.

Before the present method of genetically transforming intestinal epithelial cells and methods for providing gene therapy are described, it is to be understood that this invention is not limited to the particular methodology, protocols, cell lines, intestinal cells, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "an intestinal epithelial cell" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions

By "intestine" is meant the lower part of the alimentary canal, which extends from the stomach to the anus and is composed of a convoluted upper part (small intestine) and a lower part of greater diameter (large intestine).

By "small intestine" is meant the region of the intestine composed of the duodenum, jejunum, and ileum.

By "large intestine" is meant the region of the intestine composed of the ascending colon, transverse colon, descending colon, sigmoid colon, and rectum.

By "intestinal epithelial cell" is meant a cell contained within the cellular tissues that cover the lumenal surface of the intestine.

By "transformation" is meant a transient or permanent genetic change induced in a cell following incorporation of new DNA (i.e., DNA exogenous to the cell). Where the cell is a mammalian cell, the genetic change is generally achieved by introduction of the DNA into the genome of the cell.

By "naked DNA" or "naked nucleic acid" or DNA sequence and the like is meant a sequence of nucleic acid molecules that is not contained within a viral particle, bacterial cell or other encapsulating means that facilitate delivery of nucleic acid into the cytoplasm of the target cell. Naked nucleic acid can be associated with means for facilitating delivery of the nucleic acid to the site of the target cell (e.g., means that facilitate travel of the nucleic acid through the alimentary canal, protect the nucleic acid from stomach acid, and/or serve to penetrate intestinal mucus) and/or to the surface of the target epithelial cell.

By "transformed cell" is meant a cell into which (or into an ancestor of which) has been introduced, by means of recombinant nucleic acid techniques, a nucleic acid molecule, i.e., a sequence of codons formed of nucleic acids (e.g., DNA or RNA) encoding a protein of interest. The introduced nucleic acid sequence may be present as an extrachromosomal or chromosomal element.

By "DNA of interest" is meant any DNA sequence which encodes a protein or other molecule which is desirable for administration, particularly intravenous or oral administration, to a mammalian subject by gene therapy. The sequence is generally operatively linked to other sequences which are needed for its expression such as a promoter. The phrase "DNA of interest" is not meant to be limiting to DNA, but includes any nucleic acid (e.g., RNA or DNA) that encodes a protein or other molecule desirable for administration.

By "protein" is meant a polypeptide (native (i.e., naturally-occurring) or mutant), oligopeptide, peptide, or other amino acid sequence. As used herein, "protein" is not limited to native or full-length proteins, but is meant to encompass protein fragments having a desired activity or other desirable biological characteristic, as well as mutants or derivatives of such proteins or protein fragments that retain a desired activity or other biological characteristic. Mutant proteins encompass proteins having an amino acid sequence that is altered relative to the native protein from which it is derived, where the alterations can include amino acid substitutions (conservative or non-conservative), deletions, or additions (e.g., as in a fusion protein).

By "promoter" is meant a minimal DNA sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

By "intestinal cell specific promoter" is meant a promoter which directs expression of an operably linked DNA sequence when bound by transcriptional activator proteins, or other regulators of transcription, which are unique to an intestinal cell (e.g., an intestinal epithelial cell, or a specific type of intestinal epithelial cell (e.g., small intestine cell, large intestine cell, glandular cell, or absorptive cell)). For example, by "intestinal cell specific promoter" is meant a intestinal cell specific promoter that directs expression in an intestinal epithelial cell such as promoters for sucrase, lactase-phlorizin hydrolase, and carbonic anhydrase. Exemplary intestinal cell promoters are described in Boll et al. 1991 *Am. J. Hum. Genet.* 48:889–902; Brady et al. 1991 *Biochem. J.* 277:903–5; Drummond et al. 1996 *Eur. J. Biochem.* 236:670–81; Olsen et al. 1994 *FEBS Lett.* 342:325–8; Rodolosse et al. 1996 *Biochem. J.* 315:301–6; Sowden et al. 1993 *Differentiation* 53:67–74; Traber 1990 *Biochem. Biophys. Res. Commun.* 173:765–73; Traber et al. 1992 *Mol. Cell. Biol.* 12:3614–27; Troelsen et al. 1994 *FEBS Lett.* 342:291–6; Troelsen et al. 1994 *FEBS Lett.* 342:297–301; and Troelsen et al. 1992 *J. Biol. Chem.* 267:20407–11.

By "operably linked" is meant that a DNA coding sequence and a regulatory sequence(s) are connected in such a way as to permit gene expression of the coding sequence when the appropriate molecules (e.g., transcriptional activator proteins) are bound to the regulatory sequence(s).

By "operatively inserted" is meant that the DNA of interest introduced into the cell is positioned adjacent a DNA sequence which directs transcription and translation of the introduced DNA (i.e., facilitates the production of, e.g., a polypeptide encoded by a DNA of interest) and is thus positioned so that the coding sequence is expressed.

By "mammalian subject" or "mammalian patient" is meant any mammal for which gene therapy is desired, including human, porcine, bovine, equine, canine, and feline subjects.

By "substantially free" (e.g., as used in the phrase "substantially free of lipofectin, dendrimer, or viral particles" (especially viral particles capable of introducing a nucleic acid sequence into a host cell)) is meant containing relatively little or substantially none of the recited compound or agent, e.g., the formulation contains relatively little or substantially none of the recited compound or agent, e.g., the recited compound or agent is present as less than 5% of the total composition, preferably less then 1%, more preferably less than 0.1%, most preferably less than 0.01% to 0.001% to undetectable or contaminating levels.

General Aspects

The present invention features compositions and methods of treatment using gene therapy, more specifically gene therapy by expression of a DNA of interest in cells within the intestine of a mammalian patient. Preferably, the transformed intestinal cells expressing the protein encoded by the DNA of interest secrete a therapeutically effective amount of the protein into the blood stream or into the gastrointestinal tract of the mammalian patient. Preferably, the intestinal cell into which the DNA of interest is introduced and expressed is an epithelial cell of the intestine, and may be an intestinal cell of either the small or large intestine. Preferably, the DNA of interest encodes either insulin, a growth hormone, clotting factor VIII, intrinsic factor, erythropoietin, Factor IX, and all other blood factors that may be lacking, e.g., plasma proteins, hormones or plasma protease inhibitors. Where the target of gene therapy is the gastrointestinal tract, the DNA of interest can encode phenylalanine transporter (for phenylketonuria), lactase for lactase deficiency, intrinsic factor, or other brush border enzymes and transporters. Preferably, the DNA of interest is operably linked to a promoter capable of expressing the gene of interest at adequate levels. Promoters include both ubiquitously functioning promoters such as the viral CMV and RSV promoters or intestinal cell type specific promoters such as the sucrase or lactase promoters (Traber et al. *Molec. Cell. Biol.*, 1992, 12(8):3614–27).

The invention also features recombinant intestinal cells, preferably recombinant intestinal epithelial cells, more preferably recombinant small intestine epithelial cells or large intestine epithelial cells, containing a DNA of interest operatively inserted in the genome of the cell and operatively linked to a promoter for expression of the DNA of interest. Preferably, the promoter operatively linked to the DNA of interest is a promoter capable of expressing the gene of interest at adequate levels. Promoters include both ubiquitously functioning promoters such as the viral CMV and RSV promoters or intestinal cell type specific promoters such as the sucrase or lactase promoters (Traber et al. *Molec. Cell. Biol.*, 1992, 12(8):3614–27).

The invention will now be described in further detail.

Vectors and Constructs

Any nucleic acid vector having a eukaryotic promoter operably linked to a DNA of interest can be used in the invention to transform an intestinal cell. The vectors containing the DNA sequence (or the corresponding RNA sequence) which may be used in accordance with the invention may be any eukaryotic expression vector containing the DNA or the RNA sequence of interest. For example, a plasmid can be cleaved to provide linear DNA having ligatable termini. These termini are bound to exogenous DNA having complementary, like ligatable termini to provide a biologically functional recombinant DNA molecule having an intact replicon and a desired phenotypic property.

Techniques for production of nucleic acid constructs for expression of exogenous DNA or RNA sequences in a host are known in the art (see, for example, Kormal et al., *Proc. Natl. Acad. Sci. USA*, 84:2150–2154, 1987; Sambrook et al. *Molecular Cloning: A Laboratory Manual*, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Various vectors (e.g., bacterial vectors, or vectors capable of replication in eukaryotic and prokaryotic hosts) can be used in accordance with the present invention. Preferably the vector is capable of replication in both eukaryotic and prokaryotic hosts. Numerous vectors which can replicate in eukaryotic and prokaryotic hosts are known in the art and are commercially available. In general, such vectors used in accordance with the invention are composed of a bacterial origin of replication and a eukaryotic promoter operably linked to a DNA of interest.

Preferably, the DNA construct contains a promoter to facilitate expression of the DNA of interest within an intestinal epithelial cell. Preferably the promoter is a strong, eukaryotic promoter. Exemplary eukaryotic promoters for facilitating transcription in a eukaryotic cell include promoters from cytomegalovirus (CMV), mouse mammary tumor virus (MMTV), Rous sarcoma virus (RSV), and adenovirus. More specifically, exemplary promoters include the promoter from the immediate early gene of human CMV (Boshart et al., *Cell* 41:521–530, 1985) and the promoter from the long terminal repeat (LTR) of RSV (Gorman et al., *Proc. Natl. Acad. Sci. USA* 79:6777–6781, 1982). Of these two promoters, the CMV promoter is preferred as it provides for higher levels of expression than the RSV promoter.

For eukaryotic expression (e.g., in an intestinal epithelial cell), the construct preferably comprises at least a eukaryotic promoter operably linked to a DNA of interest, which is in turn operably linked to a polyadenylation sequence. The polyadenylation signal sequence may be selected from any of a variety of polyadenylation signal sequences known in the art. Preferably, the polyadenylation signal sequence is the SV40 late polyadenylation signal sequence. The construct may also include sequences in addition to promoters which enhance expression in intestinal epithelial cells (e.g., enhancer sequences, introns). For example, the construct can include one or more introns, which can increase levels of expression of the DNA of interest, particularly where the DNA of interest is a cDNA (e.g., contains no introns of the naturally-occurring sequence). Any of a variety of introns known in the art may be used. Preferably, the intron is the human β-globin intron and inserted in the construct at a position 5' to the DNA of interest.

Other components such as a marker (e.g., an antibiotic resistance gene (such as an ampicillin resistance gene) or β-galactosidase) to aid in selection of cells containing and/or expressing the construct (e.g., during the process of vector construction), an origin of replication for stable replication of the construct in a bacterial cell (preferably, a high copy number origin of replication), a nuclear localization signal, or other elements which facilitate production of the DNA construct, the protein encoded thereby, or both. A schematic of an exemplary construct useful in the method of the invention is shown FIG. 1.

Therapeutic Gene Products and Conditions Amenable to Treatment by Intestinal Cell Gene Therapy The DNA of interest can be any exogenous DNA sequence encoding any protein for which intravenous therapy and/or therapy for the gastrointestinal tract is desirable. For example, intravenous protein therapy is appropriate in treating a mammalian subject having an inherited or acquired disease associated with a specific protein deficiency (e.g., diabetes, hemophilia, anemia, severe combined immunodeficiency). Such protein deficient states are amenable to treatment by replacement therapy, i.e., expression of a protein to restore the blood stream levels of the protein to at least normal levels. Secretion of a therapeutic protein into the gastrointestinal tract (e.g. by secretion of the protein into the mucosal secretion) is appropriate where, for example, the subject suffers from a protein deficiency associated with absorption of nutrients (e.g. deficiency in intrinsic factor, sucrase, lactase, digestive enzymes, or transporters).

Alternatively, the mammalian subject may have a condition which is amenable to treatment by expression or overexpression of a protein which is either normally present in a healthy mammalian subject or is foreign to the mammalian subject. For example, intravenous protein therapy can be used in treatment of a mammalian subject having a viral (e.g., human immunodeficiency virus (HIV), Epstein-Barr virus (EBV), or herpes simplex virus (HSV)), bacterial, fungal, and/or parasitic infection, particularly where the infection is chronic, i.e., persisting over a relatively long period of time. The intestinal cell gene therapy of the invention may also be used to enhance expression of a protein present in a normal mammal, or to express a protein not normally present in a normal mammal, in order to achieve a desired effect (e.g., to enhance a normal metabolic process). For example, cells of the intestinal tract of a dairy cow may be transformed with DNA encoding bovine growth hormone (EGH) in order to enhance levels of BGH in the blood stream and enhance milk production.

The DNA of interest is preferably obtained from a source of the same species as the mammalian subject to be treated (e.g. human to human), but this is not an absolute requirement. DNA obtained from a species different from the mammalian subject can also be used, particularly where the amino acid sequences of the proteins are highly conserved and the xenogeneic protein is not highly immunogenic so as to elicit a significant, undesirable antibody response against the protein in the mammalian host. Further, the DNA can be synthetically produced via chemical synthesis and/or via genetic engineering in cells.

Exemplary, preferred DNAs of interest include recombinant or isolated DNA sequences encoding insulin, growth hormone, clotting factor VIII, intrinsic factor, and erythropoietin. Of particular interest is intravenous protein therapy of a mammalian subject (e.g., a bovine, canine, feline, equine, or human subject, preferably a bovine or human subject, more preferably a human subject) by expression of DNA encoding a protein (e.g., insulin, growth hormone, clotting factor VIII, or erythropoietin) in a transformed mammalian intestinal cell. Preferably, the subject is a human subject and the DNA expressed encodes a human protein (e.g., human insulin, human growth hormone, human clotting factor VIII, or human erythropoietin). Other exemplary DNAs of interest include tissue plasminogen activator (tPA), urokinase, streptokinase, acidic fibroblast growth factor, basic fibroblast growth factor, tumor necrosis factor alpha, tumor necrosis factor β, transforming growth factor β, platelet-derived growth factor, endothelian, and soluble CD4. In general, the DNAs of interest can be a sequence encoding a gene that decreases production of a gene product (e.g., genes involved in lipoprotein production by intestines) or can be nucleic acids that do not encode genes (e.g., ribozymes or antisense nucleic acids) but that are useful for decreasing lipoprotein production by the intestines. The DNAs of interest can also be synthetic nucleic acids, e.g., modified synthetic bases that can alter sensitivity of the DNA of interest to endogenous nucleases or increase cellular uptake. The DNAs of interest can encode a gene product for immunotherapy, which can facilitate development of immunity to infection, or development of tolerance to treat autoimmune disease, as in type I diabetes mellitus or rheumatoid arthritis. Table 1 provides a list of exemplary proteins and protein classes which can be delivered by the intestinal cell gene therapy of the invention.

TABLE 1

Exemplary Proteins and Protein Classes for Intestinal Cell Gene Therapy

SPECIFIC EXEMPLARY PROTEINS

| | |
|---|---|
| insulin | interferon-α2B |
| human growth hormone (hGH) | transforming growth factor (TGF) |
| erythropoietin (EPO) | ciliary neurite transforming factor (CNTF) |
| clotting factor VIII | insulin-like growth factor-1 (IGF-1) |
| bovine growth hormone (BGH) | granulocyte macrophage colony stimulating factor (GM-CSF) |
| platelet derived growth factor (PDGF) | interferon-α2A |
| clotting factor VIII | brain-derived neurite factor (BDNF) |
| thrombopoietin (TPO) | insulintropin |
| IL-1 | tissue plasminogen activator (tPA) |
| IL-2 | urokinase |
| IL-1 RA | streptokinase |
| superoxide dismutase (SOD) | adenosine deamidase |
| catalase | calcitonin |
| fibroblast growth factor (FGF) (acidic or basic) | arginase |
| neurite growth factor (NGF) | phenylalanine ammonia lyase |
| granulocyte colony stimulating factor (G-CSF) | γ-interferon |
| L-asparaginase | pepsin |
| uricase | trypsin |
| chymotrypsin | elastase |
| carboxypeptidase | lactase |
| sucrase | intrinsic factor |
| calcitonin | parathyroid hormone (PTH)-like hormone |
| | cholecystokinin (CCK) |
| Ob gene product | |
| glucagon | insulinotrophic hormone |
| glucagon-like-peptide I (GLP-1) | |

TABLE 1-continued

Exemplary Proteins and Protein Classes for Intestinal Cell Gene Therapy

EXEMPLARY CLASSES OF PROTEINS

| | |
|---|---|
| proteases | pituitary hormones |
| protease inhibitors | growth factors |
| cytokines | somatomedians |
| chemokines | immunoglobulins |
| gonadotrophins | interleukins |
| chemotactins | interferons |
| lipid-binding proteins | |

Various disease conditions are amenable to treatment using the intestinal cell gene therapy of the invention. One skilled in the art can recognize the appropriate protein that should be produced by the invention for treating specific disease conditions. Exemplary diseases that are amenable to treatment using the subject invention, and exemplary, appropriate proteins which can be used in treating these diseases, are shown in Table 2.

TABLE 2

Exemplary Disease Conditions Amenable to Intestinal Cell Gene Therapy

| | |
|---|---|
| Enzyme Deficiency | Endotoxic Shock/Sepsis |
| Adenosine deaminase[1] | Lipid-binding protein (LBP) |
| Purine nucleotide phosphorylase | |
| Galactosidase | |
| β-glucuronidase | |
| Antioxidants for Cancer Therapy | Anemia |
| Superoxide dismutase | Erythropoietin |
| Catalase | |
| | Growth Factors (for use in wound healing, induction of red blood cell formation, etc.) |
| Cancer | |
| α-Interferon | Epidermal growth factor |
| β-Interferon | G-CSF |
| α-IL1 | γ-Interferon |
| Phenylalanine ammonia lyase | Transforming growth factor |
| Arginase | Erythropoietin |
| L-asparaginase | Thrombopoietin |
| Uricase | Insulin-like growth factor-1 |
| Granulocyte colony stimulating factor (G-CSF) | Insulin |
| Monoclonal antibodies | Human growth hormone |
| Tissue necrosis factor | |
| Cardiovascular Disease | Diabetes |
| Tissue plasminogen activator | Insulin |
| Urokinase (native or chimeric) | Glucagon |
| α₁-antitrypsin | Insulinotrophic hormone |
| Antithrombin-III | Clotting disorders |
| Other proteases or protease inhibitors | Clotting factor VIII |
| Apolipoproteins (particularly B-48) | |
| Circulating Scavenger Receptor APO A1[2] | |
| | Gastrointestinal and Pancreatic Deficiencies |
| Obesity and Feeding | |
| Ob gene product | Pepsin (for esophageal reflux) |
| Cholecystokinin (CCK) | Trypsin |
| | Chymotrypsin |
| | Elastase |
| Bone diseases | Carboxypeptidase |

TABLE 2-continued

Exemplary Disease Conditions Amenable to
Intestinal Cell Gene Therapy

| | |
|---|---|
| Calcitonin | Lactase (for lactose deficiency) |
| PTH-like hormone | Sucrase |
| | Intrinsic Factor (pernicious anemia) |

Organ-Specific Autoimmune diseases (target of antibody in parentheses)

Myasthenia gravis (acetylcholine receptors)
Graves' disease (thyroid-stimulating hormone receptor)
Thyroiditis (thyroid, peroxidase)
Insulin-resistant diabetes with acanthosis nigricans or
with ataxia telangiectasia (Insulin receptor)
Allergic rhinitis, asthma (Beta$_2$-adrenergic receptors)
Juvenile insulin-dependent diabetes (insulin, GAD65)
Pernicious anemia (gastric parietal cells, vitamin B$_{12}$
binding site of intrinsic factor)
Addison's disease (adrenal cells)
Idiopathic hypoparathyroidism (parathyroid cells)
Spontaneous infertility (sperm)
Premature ovarian failure (interstitial cells, corpus luteum cells)
Pemphigus (intercellular substance of skin and mucosa)
Bullous pemphigoid (basement membrane zone of skin and mucosa)
Primary biliary cirrhosis (mitochondria)
Autoimmune hemolytic anemia (erythrocytes)
Idiopathic thrombocytopenic purpura (platelet)
Idiopathic neutropenia (neutrophils)
Vitiligo (melanocytes)
Osteosclerosis and Meniere's disease (type II collagen)
Chronic active hepatitis (nuclei of hepatocytes)

Systemic Autoimmune Diseases (defect/organ affected in parentheses)

Goodpasture's syndrome (basement membranes)
Rheumatoid arthritis (γ-globulin, EBV-related antigens, collagen types II
and III
Sjögren's syndrome (γ-globulin, SS-A (Ro), SS-B (La)
Systemic lupus erythematosus (nuclei, double-stranded DNA, single-
stranded
DNA, Sm ribonucleoprotein, lymphocytes, erythrocytes, neurons,
γ-globulin)
Scleroderm (nuclei, Scl-70, SS-A (Ro), SS-B (La), centromere
Polymyositis (nuclei, Jo-1, PL-7, histadyl-tRNA synthetase,
threonyl-tRNA synthetase, PM-1, Mi-2
Rheumatic fever (myocardium heart valves, choroid plexus)

[1]For treatment of severe combined immunodeficiency
[2]Converts low-density lipoproteins to high-density lipoproteins Numerous proteins that are desirable for intravenous protein therapy are well known in the art and the DNA encoding these proteins has been isolated. For example, the sequence of the DNAs encoding insulin, human growth hormone, intrinsic factor, clotting factor VIII, and erythropoietin are available from GenBank and/or have been described in the scientific literature (e.g., human clotting factor VIII gene: Gitschier et al., *Nature* 312:326–330, 1984; Wood et al., *Nature* 312:330–337, 1984; human intrinsic factor: Hewitt et al., *Genomics* 10:432–440, 1991). Proteins commonly used in treatments can be used in the gene therapy procedures of the present invention. Such proteins are disclosed in, for example, the Physicians' Desk Reference (1994 Physicians' Desk Reference, 48th Ed., Medical Economics Data Production Co., Montvale, N.J.; incorporated by reference) and can be dosed using methods described in Harrison's Principles of Internal Medicine and/or the AMA "Drug Evaluations Annual" 1993, all incorporated by reference.

Where the DNA encoding a protein of interest has not been isolated, this can be accomplished by various, standard protocols well known to those of skill in the art (see, for example, Sambrook et al., ibid; Suggs et al., *Proc. Natl. Acad. Sci. USA* 78:6613–6617, 1981; U.S. Pat. No. 4,394,443; each of which are incorporated herein by reference with respect to identification and isolation of DNA encoding a protein of interest). For example, genomic or cDNA clones encoding a specific protein can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (U.S. Pat. Nos. 4,683,195 and 4,683,202). Nucleotide substitutions, deletions, additions, and the like can also be incorporated into the polynucleotides, so long as the ability of the polynucleotide to hybridize is not substantially disrupted (Sambrook et al. ibid). The clones can be expressed or the DNA of interest can be excised or synthesized for use in other constructs. If desired, the DNA of interest can be sequenced using methods well known in the art.

In a preferred embodiment, the construct used in the present invention is designed so as to enhance protein secretion from the transformed intestinal epithelial cell into the blood stream. Intestinal epithelial cells are normally polarized, with the apical surface oriented toward the lumen of the gastrointestinal tract and the basolateral surface oriented toward the blood supply.

The intestinal epithelium is the major absorptive surface in animals, and as such transports substances preferentially from the intestinal lumen into blood. Although these processes have been most widely studied for hexoses, amino acids and electrolytes, it has become increasingly clear that larger molecules are absorbed as well. For example, small polypeptides are absorbed into absorptive cells, and in newborn animals antigenicity is achieved as the result of the absorption of maternal antibody proteins. There is also a variety of evidence that various digestive enzymes from the pancreas, as well as other large molecules such as insulin and albumin, cross the intestinal epithelium at substantial rates (see references). Indeed, the whole plasma albumin pool leaks across the intestinal epithelium every day.

In addition, the intestines contain two types of secretory glands; ductal or exocrine glands that secrete enzymes and mucins into the intestinal lumen and endocrine glands that secrete various peptide hormones into blood. Although little is known about the mechanisms of secretion by these cells, their transfection might well lead to the secretion of the engineered protein into blood. Permeability to proteins has been seen primarily in the duodenum and terminal ileum, but proteins are also known to be absorbed from the lower portions of the large bowel, and suppositories have been used for this purpose therapeutically. For discussions of the intestinal absorption of protein, see, e.g., Liebow et al 1975 *Science* 189:472–474; Goetze et al. 1975 *Nature* 257:607–609; Goetze et al. 1976 *Lancet* ii:494–495; Goetze et al. 1978 *Biochim. Biophys. Acta* 512:214–220; Heinrich et al 1979 *Klin Wochenscht* 57:1295–1297; Lake-Bakaar et al. 1980 *Gut* 21:580–586; Martin et al. 1957 *Nature* 199:815–817; Avakian et al. 1964 *Clin. Pharmacol. Ther.* 5:712–715; Megel et al. 1964 *Arch. Biochem. Biophys.* 108:193–199; Alpers et al. 1967 *J. Biol. Chem.* 242:5617–5622; Katayama et al. 1972 *Biochim. Biophys. Acta* 288:172–180; Katayama et al. 1972 *Biochim. Biophys. Acta* 288:181–189; Urban et al. 1982 *J. Pediatr. Gastroenterol. Nutr.* 1:267–272; Katayama et al. 1968 *Biochim. Biophys. Acta* 167: 613-; Moriya et al. 1967 *Chem. Phar. Bull.* 15:1662–1668; Ambrus et al. 1967 *Clin. Pharmacol. Ther.* 8:362–368; Alpers et al. 1970 *M. Gastroenterology* 58:833–842; Brambel, F. W. R. 1958 *Biol. Rev.* 33:488-; Lev et al. 1973 *Gastroenterologia* 65:60-; Waller et al. 1972 *Nature* 177:608; Danforth et al. 1959 *Endocrinology* 65:118;

and Warshaw et al. 1974 *Gastroenterologia* 66:987. Proteins that are manufactured in the gut and targeted for secretion into the blood include hormones such as CCK (choleocystokinin), secretin, gut glucagon, vasoactive intestinal peptide (VIP), gastric inhibitory peptide (GIP), somatostatin, neuropeptide Y (NPY), islet amyloid polypeptide (IAPP), polypeptide Y (PPY), glucagon-like peptide I (GLPI), as well as a variety of lipoproteins important in lipid metabolism.

Most proteins produced by the pancreas and salivary glands are released into the duct system and eventually into the gastrointestinal tract. However, some secretory gland proteins, such as kallikreins, are secreted primarily into the blood stream. Regardless of whether a specific secretory gland protein is primarily released into the duct system or into the blood stream, there is a modest rate of transport of these same proteins into the secondary system. Secretory gland proteins are not normally partitioned solely into the blood stream or solely into the gastrointestinal tract. For example, amylase, which is primarily secreted into the duct system, is also released at a lower level into the blood stream.

The specific features responsible for mediating intravenous-directed or duct system-directed secretion have not been described. However, when salivary gland cells are transformed with DNA encoding insulin according to the present invention, relatively little insulin is released into the saliva as compared to the blood. This observation suggests that the polypeptide itself contains the information for targeting of secretion.

Preferably, the DNA of interest contains a secretion signal which either directs secretion of the protein primarily into the gastrointestinal tract or directs secretion of the protein primarily into the blood stream. Intravenous-directed secretion signals and duct system-directed secretion signals can be identified by, for example, site-directed mutagenesis of DNA encoding a blood stream-targeted protein (e.g., insulin) or a intestinal lumen-targeted protein (e.g., protease various digestive enzymes, and mucin). The mutants can be screened by expression of the mutated DNA in intestinal cells and subsequently determining the ratio of, for example, lumenal to intravenous expression. Alternatively, intravenous-directed secretion signals and intestinal lumen-directed secretion signals can also be identified by constructing recombinant, chimeric proteins composed of, for example, a putative intravenous secretion signal inserted into an intestinal lumen-directed protein. Intravenous secretion signals would then be identified by their ability to re-direct expression of the lumen-directed protein into the blood stream. Putative intravenous secretion signals and intestinal lumen secretion signals can also be identified by comparison of DNA and amino acid sequences of proteins which are preferentially secreted into either the blood stream or the gastrointestinal tract, respectively. Areas of homology or common motifs among the proteins could then be tested as described above.

The DNA of interest may be inserted into a construct so that the therapeutic protein is expressed as a fusion protein (e.g., a fusion protein having β-galactosidase or a portion thereof at the N-terminus and the therapeutic protein at the C-terminal portion). Production of a fusion protein can facilitate identification of transformed cells expressing the protein (e.g., by enzyme-linked immunosorbent assay (ELISA) using an antibody which binds to the fusion protein).

It may also be desirable to produce altered forms of the therapeutic proteins that are, for example, protease resistant or have enhanced activity relative to the wild-type protein. For example, where an enzyme is to be secreted into the gastrointestinal tract, it may be advantageous to modify the protein so that it is resistant to digestive proteases. Where a protein to be secreted requires processing that is not available in intestinal cells, the protein may be modified to allow correct processing. For example, proinsulin can be modified to allow processing to mature insulin in intestinal cells. Further, where the therapeutic protein is a hormone, it may be desirable to alter the protein's ability to form dimers or multimeric complexes. For example, insulin modified so as to prevent its dimerization has a more rapid onset of action relative to wild-type, dimerized insulin.

The construct containing the DNA of interest can also be designed so as to provide for site-specific integration into the genome of the target intestinal cell. For example, a construct can be produced such that the DNA of interest and the promoter to which it is operably linked are flanked by the position-specific integration markers of *Saccharomyces cerevisiae* Ty3. The construct for site-specific integration additionally contains DNA encoding a position-specific endonuclease which recognizes the integration markers. Such constructs take advantage of the homology between the Ty3 retrotransposon and various animal retroviruses. The Ty3 retrotransposon facilitates insertion of the DNA of interest into the 5' flanking region of many different tRNA genes, thus providing for more efficient integration of the DNA of interest without adverse effect upon the recombinant cell produced. Methods and compositions for preparation of such site-specific constructs are described in U.S. Pat. No. 5,292,662, incorporated herein by reference with respect to the construction and use of such site-specific insertion vectors.

Intravenous and Gastrointestinal Protein Therapy by Transformation of Intestinal Cells Intestinal epithelial cells transformed according to the invention facilitate expression of a DNA of interest, and can be expressed at high levels, particularly where the DNA of interest is operably linked to a strong eukaryotic promoter (e.g., CMV, MMTV promoters). The expressed protein is then secreted into the blood stream or into the gastrointestinal tract. The protein so expressed and secreted is thus useful in treating a mammalian subject having a variety of conditions. For example, secretion of an appropriate protein into the gastrointestinal tract is useful in preventing or controlling various diseases, e.g., in treating chronic infections of the small and/or large intestine (e.g., bacterial or fungal infections); in treating degenerative disorders of intestinal epithelium; in treating intestinal malabsorption syndromes (e.g., sprue); or as a replacement or supplemental protein therapy.

In a preferred embodiment, the proteins are secreted into the blood stream at levels sufficient for intravenous protein therapy. Blood stream levels of the therapeutic protein may be enhanced by integration of multiple copies of the DNA of interest into the genome of the target cells, and/or by operably linking a strong promoter (e.g., a promoter from CMV) and/or enhancer elements to the DNA of interest in the construct. Blood stream levels may also be enhanced by transformation of a greater number of target cells in the subject. As discussed above, secretion of the therapeutic protein may also be enhanced by incorporating leader sequences, amino acid sequence motifs, or other elements which mediate intravenous-directed secretion into the sequence of the therapeutic protein.

Where the present invention involves the transformation of intestinal epithelial cells, the method of intestinal in vivo gene therapy provides the additional advantage that expression of the gene product by the mammalian subject is transient due to the relatively rapid turnover rate of epithelial cells (e.g., the average life of an epithelial cell is from 2 to 4 days). Transient gene product expression in the mammalian subject allows for tight regulation of the amount of therapeutic gene product delivered to the host. Further, because the gene therapy method of the invention generally involves non-invasive methods of administration of the transforming nucleic acid, the desired therapy can be easily achieved by repeated administration. The administration of the vector to the gut can provide both short and long term effects. If mature absorptive cells are targeted, then the effect is short term (2–4 days); alternatively, if the vectors is targeted to the stem cells at the base of the villi, then long term effects should occur. Thus the method of the invention can be used to achieve both short and long term effects.

The nature of the intestinal cell transformation achieved using the in vivo gene therapy methods of the invention can be either transient or stable. By "transient transformation" is meant that the target cell expresses the gene product encoded by the introduced nucleic acid for a finite period of time, and is not expressed for the remaining life of the cell and/or the introduced nucleic acid is not passed on to one or both daughter cells following cell division. In contrast, "stable transformation" means that the cell stable expresses the introduced nucleic acid throughout the remainder of the transformed cell's life and the nucleic acid is replicated and passed on to the daughter cells after mitosis. Transient transformation is particularly advantageous where the physician desires a short period of therapy, that only a small amount of therapeutic gene product be administered, and/or if repeated, administration allows for titration of the dose. In general, as discussed above, transformation of intestinal cells according to the invention can provide short term expression of a desired gene product (e.g., 2 to 4 days) or longer term expression of a desired gene product (e.g., several days to several weeks). Preferably, expression of the DNA of interest is short term (i.e., transient).

The actual number of transformed intestinal epithelial cells required to achieve therapeutic levels of the protein of interest will vary according to several factors including the nature of the intestinal cell transformation achieved (e.g., either transient or stable transformation), the protein to be expressed, the level of expression of the protein by the transformed cells, the rate of protein secretion, the partitioning of the therapeutic protein between the gastrointestinal tract and the blood stream, and the condition to be treated. For example, the desired intravenous level of therapeutic protein can be readily calculated by determining the level of the protein present in a normal subject (for treatment of a protein deficiency), or by determining the level of protein required to effect the desired therapeutic result. The level of expression of the protein from transformed cells and the rate of protein secretion can be readily determined in vitro (e.g., by expression of the DNA of interest in an in vitro polarized cell culture such as polarized CaCo-2 cells). Given the in vitro levels of protein expression and secretion, and the estimated intravenous level of therapeutic protein desired, the number of cells which should be transformed to effect the desired levels can be readily calculated, and the gene therapy protocol carried out accordingly.

Formulations

The naked nucleic acid for in vivo transformation of intestinal cells can be formulated in a variety of ways in order to facilitate delivery of the naked nucleic acid to the surface of the intestinal cells. The form (e.g., liquid, solid, pill, capsule) and composition of he formulation will vary according to the method of administration used. For example, where the formulation is administered orally, the naked nucleic acid can be formulated as a tablet, pill, capsule, solution (e.g., gel, syrup, slurry, or suspension), or other suitable form. Where the naked nucleic acid is delivered by direct placement in the intestinal tract, the naked nucleic acid can be formulated as a suppository (e.g., for rectal administration).

The formulation can also vary with the intestinal site targeted. For example, the nuclease activity associated with the small bowel is greater than that associated with the large bowel. Thus, formulations for transformation of small bowel cells and/or formulations administered orally which must pass through the small bowel before reaching the desired target cell may contain anti-nuclease compositions to prevent degradation of the administered nucleic acid. Methods for preparation of various types of formulations, and administration of such formulations, are well known in the art (see, e.g., Remington's Pharmaceutical Sciences, Maack Publishing Co., Easton, Pa.).

The formulation can contain components in addition to the naked nucleic acid, where the additional components aid in the delivery of the naked nucleic acid to the target intestinal cell surface. The DNA of interest can be present in a pharmaceutical composition of the invention with additional components such as, but not limited to, stabilizing compounds and/or biocompatible pharmaceutical carriers, e.g., saline, buffered saline, dextrose, or water. The DNA of interest can also be administered alone or in combination with other agents, including other therapeutic agents (e.g., drugs or hormones)

Where the formulation is administered orally, the formulation can contain buffering agents or comprise a coating to protect the naked nucleic acid from stomach acidity and/or facilitate swallowing. In addition or alternatively, the oral formulation can be administered during an interdigestive period (between meals or at bedtime) when stomach pH is just slightly acidic or neutral. The formulation can also comprise a time-release capsule designed to release the nucleic acid upon reaching the surface of the target intestinal cells. For example, time-release formulations can be deigned to deliver the naked nucleic acid at a particular location within the intestine, (e.g., to deliver the nucleic acid for transformation of cells of the small intestine (naked nucleic acid released shortly after entry into the intestine)) or for transformation of cells at a lower position in the intestinal tract (e.g., cells of the large intestine). The formulation can also be designed to allow for slow release in a particular area (e.g., in the absence of peristalsis). The formulation can also comprise nuclease inhibitors to enhance the amount of intact nucleic acid available for transformation of the target intestinal cells.

The DNA of interest can be formulated as a DNA- or RNA-liposome complex formulation. Such complexes comprise a mixture of lipids which bind to genetic material (DNA or RNA), providing a hydrophobic coat which allows the genetic material to be delivered into cells. Liposomes that can be used in accordance with the invention include DOPE (dioleyl phosphatidyl ethanol amine), CUDMEDA (N-(5-cholestrum-3-β-ol 3-urethanyl)-N',N'-dimethylethylene diamine). When the DNA of interest is introduced using a liposome, it is preferable to first determine in vitro the optimal values for the DNA:lipid ratios and the absolute concentrations of DNA and lipid as a function of cell death and transformation efficiency for the particular type of cell to be transformed. These values can then be used in or extrapolated for use in in vivo transformation. The in vitro determinations of these values can be readily carried out using techniques which are well known in the art.

Other formulations that can also be used in accordance with the present invention. Such formulations include DNA or RNA coupled to a carrier molecule (e.g., an antibody or a receptor ligand) which facilitates delivery to host cells for the purpose of altering the biological properties of the host cells. By the term "chemical modification" is meant modifications of nucleic acids to allow, for example, coupling of the nucleic acid compounds to a carrier molecule such as a protein or lipid, or derivative thereof. Exemplary protein carrier molecules include antibodies specific to the cells of a targeted intestinal cell or receptor ligands, i.e., molecules capable of interacting with receptors associated with a cell of a targeted intestinal cell.

In general, the formulation is preferably primarily composed of naked DNA (e.g., DNA that is not contained within a viral particle) and is substantially free of detergent (e.g., polybrene) or mucolytic agents (e.g., N-acetylcysteine, dithiothreitol, pepsin, and pilocarpine). Further, the formulation for transformation of intestinal cells according to the invention preferably is substantially free of proliferation enhancing factors (e.g., factors that enhance uptake of nucleic acid into cells that do not divide rapidly) such as epidermal growth fact, angiogenesis factor, insulin-like growth factor-1, insulin-like growth factor-2, transforming growth factor-$\alpha$, gastrin, methotrexate, fluorouracil, floxuridine, and arabinoside-C. Preferably, the formulation is prepared to target epithelial cells of the intestine, more preferably intestinal cells other than intestinal stem cells.

Administration and In Vivo Transformation of Intestinal Cells

Gastrointestinal administration of the DNA of interest can be accomplished by a variety of methods well known in the art. In general, the methods useful in connection with the present invention involve the exposure of the targeted cells of the intestine (e.g., intestinal epithelial cells, specifically epithelial cells of the small or large intestine) to a formulation comprising nucleic acid encoding a therapeutic gene product of interest. Such methods include, but are not limited to, oral administration and direct administration of the nucleic acid to the lumen of the intestine through use of, for example, a suppository, endoscope, or catheter. Preferably, the nucleic acid is administered to the subject orally.

The amount of DNA to transform a sufficient number of the targeted intestinal cells and provide for expression of therapeutic levels of the protein can be readily determined based upon such factors as the efficiency of in vivo transformation in animal models, the levels of protein expression achieved in vitro and/or in vivo, and the susceptibility of the targeted intestinal cells to transformation. For example, where the targeted intestinal cell is a small intestine epithelial cell and the nucleic acid is administered orally as naked DNA, the naked DNA is administered at a concentration sufficient to reach the small intestine to provide a DNA concentration effective to transform the targeted small intestine epithelial cells and provide for therapeutic levels of the protein in either the blood or the gastrointestinal tract. In general, the nucleic acid is administered ranging from about 1 mg to 1 gram, generally about 100 mg to about 1 gram, depending on the formulation used. The formulation can be administered, for example, several times daily, daily, or several times a week, depending upon the desired level of protein expression desired and/or the period over which therapy is desired.

Overall secretion from intestinal epithelial cells may be augmented by hormonal stimulation. For example, where the protein is primarily secreted into the gastrointestinal tract and is secreted at lower levels into the blood stream, hormonal stimulation may enhance both gastrointestinal and intravenous secretion. Thus, therapeutically effective levels of the protein in the gastrointestinal tract and the blood stream may be achieved or enhanced by administration of an appropriate, intestine-specific hormone. For example, cholinergic and CCK-mediated stimulation enhances secretion from intestinal glands. Alternatively, overall secretion by intestinal cells can be regulated by ingestion of certain foodstuffs. Ingestion of certain foodstuffs is associated with augmented expression of brush border enzymes such as sucrase and lactase. Thus, increased expression of the protein(s) of interest delivered using the intestinal gene therapy method of the invention can also be increased by regulation or modification of the subject's diet.

Assessment of Protein Therapy

Following transfer of a DNA of interest into intestinal epithelial cells, the effects of expression of the protein encoded by the DNA of interest can be monitored in a variety of ways. Generally, a sample of blood or a sample of intestinal mucosal secretions from the subject can be assayed for the presence of the therapeutic protein. Appropriate assays for detecting a protein of interest in such samples are well known in the art. For example, where intestinal cell gene therapy has been performed to accomplish intravenous protein therapy, a sample of blood can be tested for the presence of the protein using an antibody which specifically binds the therapeutic protein in an ELISA assay. This assay can be performed either qualitatively or quantitatively. The ELISA assay, as well as other immunological assays for detecting a protein in a sample, are described in *Antibodies: A Laboratory Manual* (1988, Harlow and Lane, ed.s Cold Spring Harbor Laboratory, Cold Spring Harbor, N.Y.).

Alternatively, or in addition, the efficacy of the protein therapy can be assessed by testing a sample of blood or intestinal secretion for an activity associated with the therapeutic protein (e.g., an enzymatic activity). For example, where the therapeutic protein has antimicrobial activity, the efficacy of therapy can be tested by examining the ability of the test sample to inhibit bacterial growth. Furthermore, the efficacy of intestinal cell gene therapy can be assessed by monitoring the condition of the mammalian subject for improvement. For example, where the therapeutic protein is erythropoietin, the subject's blood is examined for iron content or other parameters associated with anemia. Where the therapeutic protein is insulin, the efficacy of the therapy can be assessed by examining blood glucose levels of the mammalian subject or by measuring insulin (e.g., by using the human insulin radioimmunoassay kit, Linco Research Inc., St. Louis, Mo.).

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Figure 2:
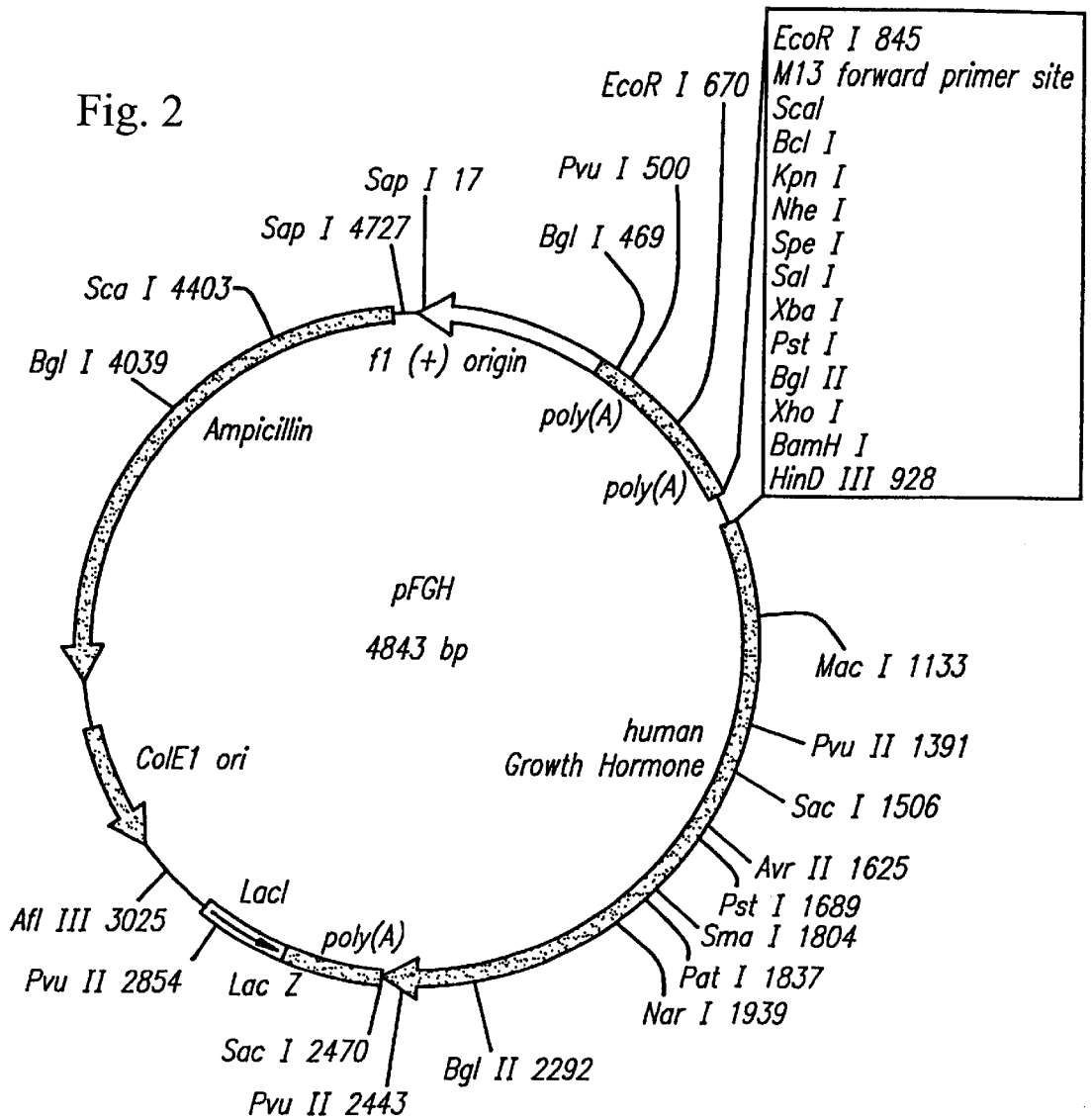
FIG. 2 is a map of the pFGH construct, which contains the human growth hormone genomic sequence.
Figure 3:
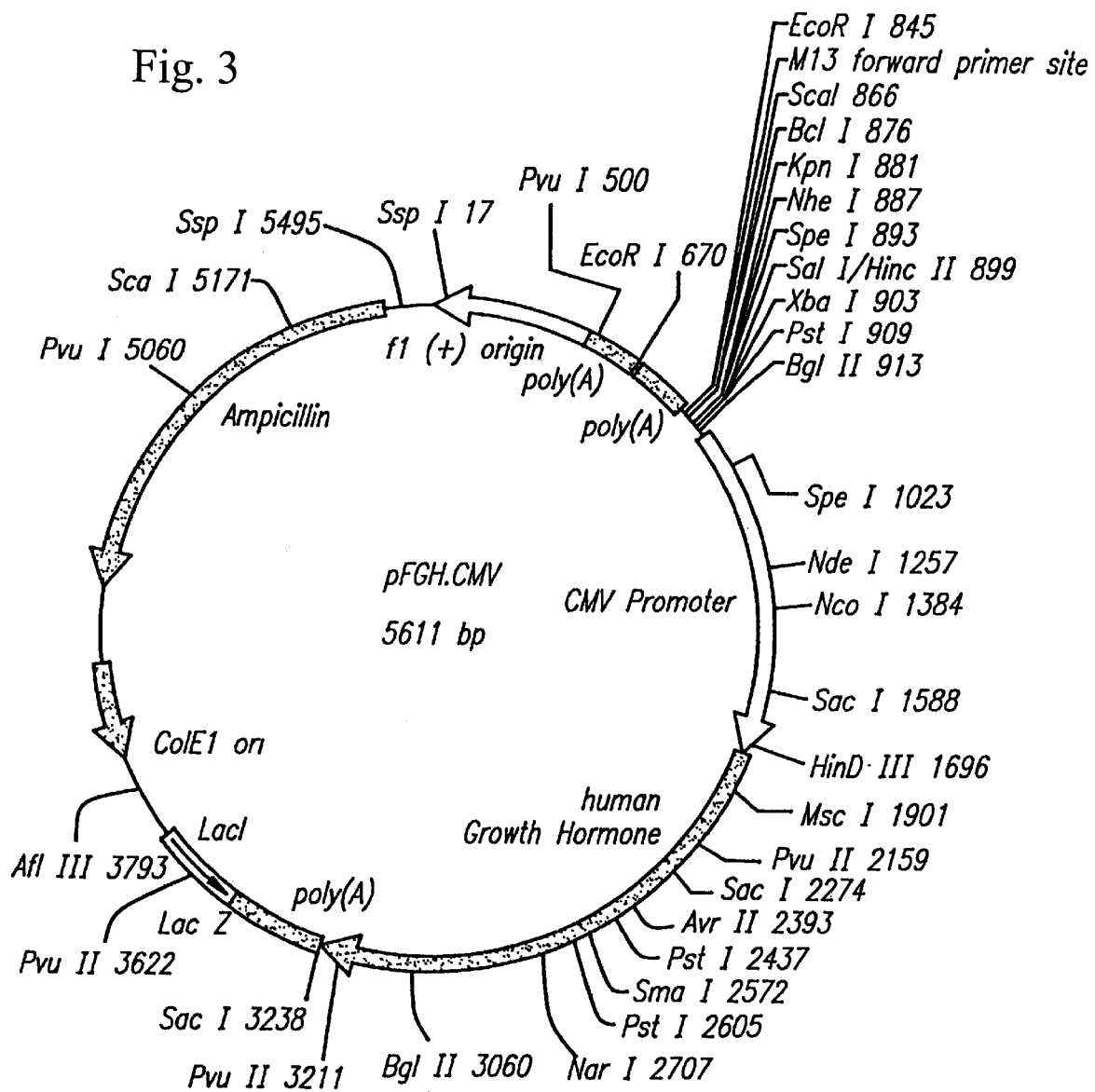
FIG. 3 is a map of the pFGH.CMV construct, which contains the human growth hormone genomic sequence operably linked to the CMV promoter.
Figure 4:
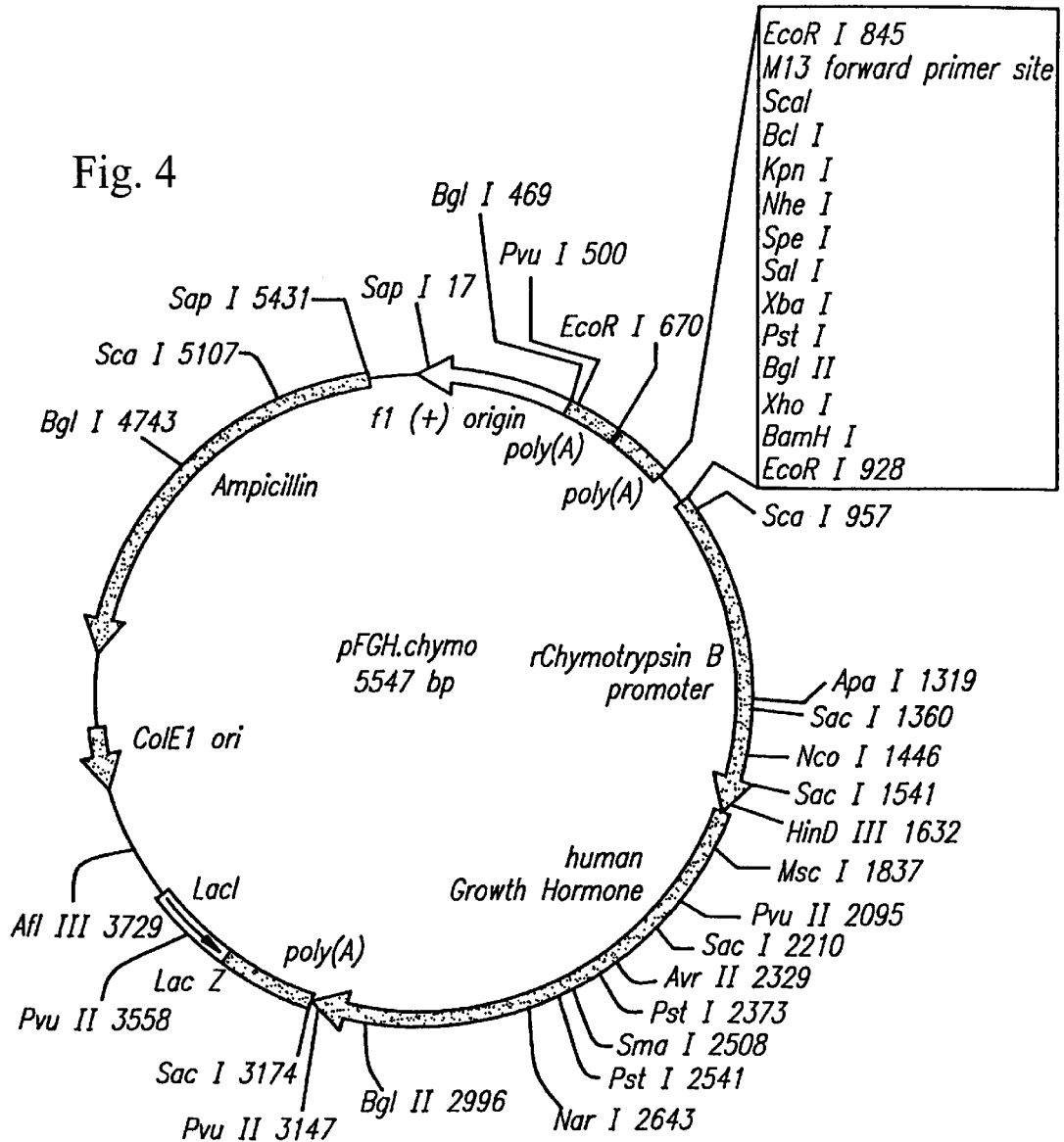
FIG. 4 is a map of the pFGH.chymo construct, which contains the human growth hormone genomic sequence operably linked to the chymotrypsin B promoter.

Example 1
Construction of Vectors Expressing Human Growth Hormone (hGH) for Intestinal Cell Transformation Four constructs for expression of human growth hormone (hGH) were prepared using techniques well known in the art (see, for example, Sambrook et al. ibid). The first construct, PFGH, contains the genomic hGH DNA sequence inserted in the commercially available vector PBLUESCRIPT SK+™ (Stratagene, La Jolla Calif.) (FIG. 2). Because the hGH coding sequence is not linked to a promoter, this vector provides for no or only low-level hGH expression. Thus, the pFGH construct serves as a negative control for hGH expression in the intestine. The second construct, pFGH.CMV, was constructed by operably inserting the promoter from the immediate early gene of human CMV upstream of the genomic hGH sequence of the pFGH vector (FIG. 3). The third construct, pFGH.chymo, was constructed by operably inserting the rat chymotrypsin B gene promoter upstream of the genomic hGH sequence of the pFGH vector (FIG. 4). The fourth construct, pFGH.RSV, was constructed by operably inserting the promoter from the long terminal repeat (LTR) of RSV upstream of the genomic hGH sequence of the PFGH vector.

Example 2
In Vivo Gene Transfer of DNA Encoding Human Growth Hormone by Introduction of Naked DNA into the Intestinal Lumen pFGH.CMV was used to transform intestinal epithelium of approximately 300 g adult rats (PFGH.CMV 10 rats; pFGH.CMV with lipofectin, 4 rats; PFGH.CMV with polycationic dendrimers, 4 rats; negative control (PBS), 1 rat; and negative control (no surgery), 8 rats.

The rats were anesthetized with pentobarbital. A laparotomy was performed and the upper duodenum or terminal ileum identified. A 5 cm length of intestine was ligated, a small aliquot of venous blood was obtained, and 400 $\mu$l of phosphate-buffered saline (PBS) containing PFGH.CMV, or 400 $\mu$l of PBS alone (negative control no. 1), were slowly injected or infused into the intestine and left in place for 15 min. The amount of solution used produces a slight expansion of the bowel. The vector-containing solutions were composed of 20–200 $\mu$g DNA per 400 $\mu$l in PBS; 32 $\mu$g DNA per 400 $\mu$l in PBS with 6% lipofectin (a cationic lipid used to increase transformation efficiency); or 32 $\mu$g DNA per 100 $\mu$l in PBS with 128 $\mu$g of dendrimers. The elastic ties were then removed, the bowel replaced in its normal location, and the abdomen closed with sutures. Recovery after surgery was nominal, and no sign or symptoms of disease were noticed over the next 48 hours. At autopsy, the intestine looked normal in all respects. This transfection method provides direct access of the vector to over 5–10% of the intestinal cells.

After 24 hours, the rats were again anesthetized with pentobarbital, tissue extracted, and a sample of blood taken prior to sacrifice. The blood samples from before and after transfection were prepared, growth hormone measured in each sample using an immunoassay for hGH. The levels of hGH in the serum samples were measured using the hGH radioimmune assay (Nichols Institute) except that bound samples were washed three times and placed into new tubes prior to gamma counting. Each assay was performed in triplicate and compared to a set of control samples.

Figure 5:
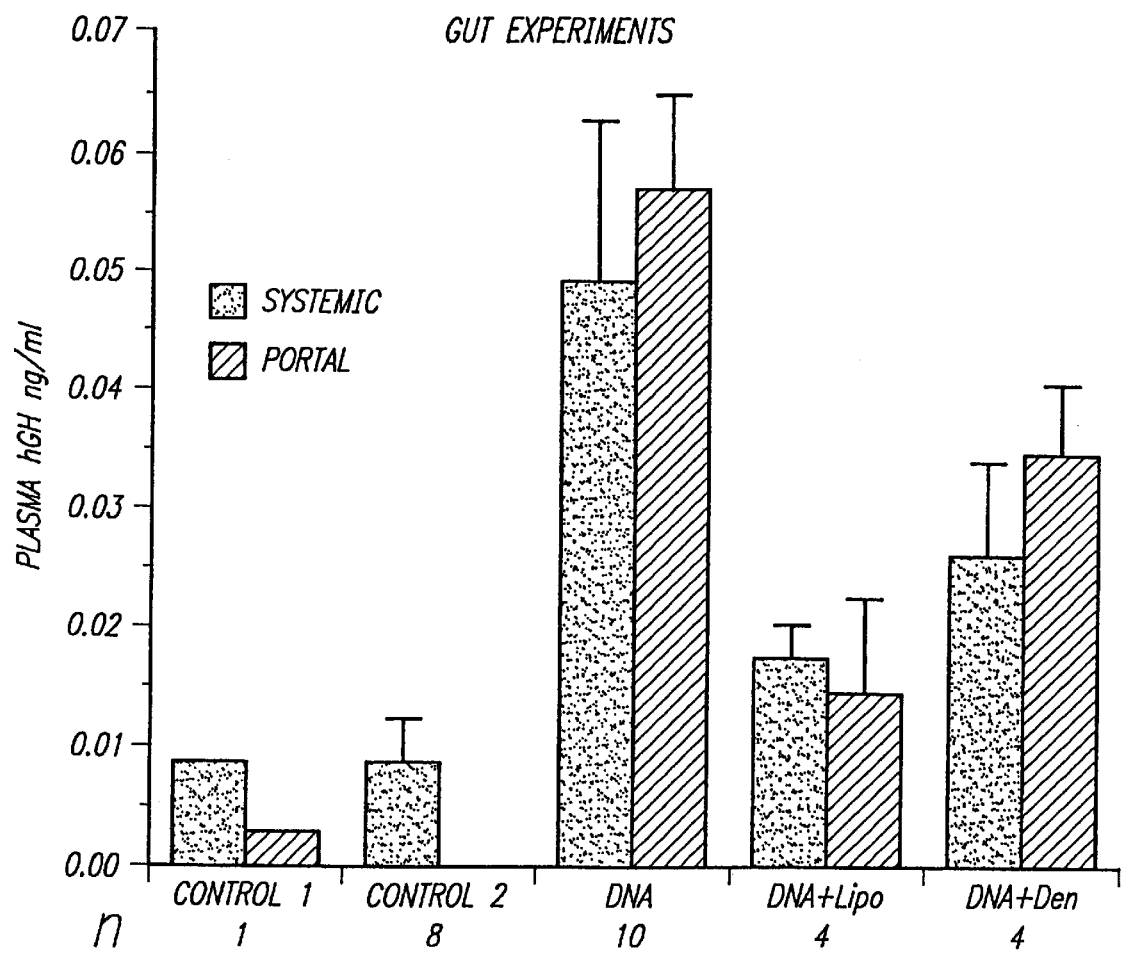
FIG. 5 is a graph showing the levels of human growth hormone in systemic blood (filled bars) and portal vein blood (hatched bars) after exposure of intestinal segments to a solution composed of DNA encoding human growth hormone.

Rats receiving the PFGH.CMV vector alone (naked DNA) expressed higher levels of hGH in samples of systemic and portal vein blood (FIG. 5), compared to background levels of hGH cross-reactivity in rats receiving no DNA. The addition of lipofectin did not increase transformation efficiency (as measured by the presence of hGH in the blood samples), but rather significantly decreased transformation efficiency relative to use of naked DNA. Likewise, transformation efficiency in rats receiving DNA plus dendrimers was decreased relative to use of naked DNA alone. Thus, administration of naked DNA encoding hGH in a simple PBS solution not only resulted in successful transformation of intestinal cells, but also resulted in more efficient intestinal cell transformation and subsequent hGH intravenous secretion than administration of the same construct in a formulation containing lipofectin or dendrimers. Furthermore, plasma levels were similarly elevated after both duodenal and ileal administration, indicating that intestinal cell transformation was achieved at similar levels of efficiency at these two sites.

Figure 6A:
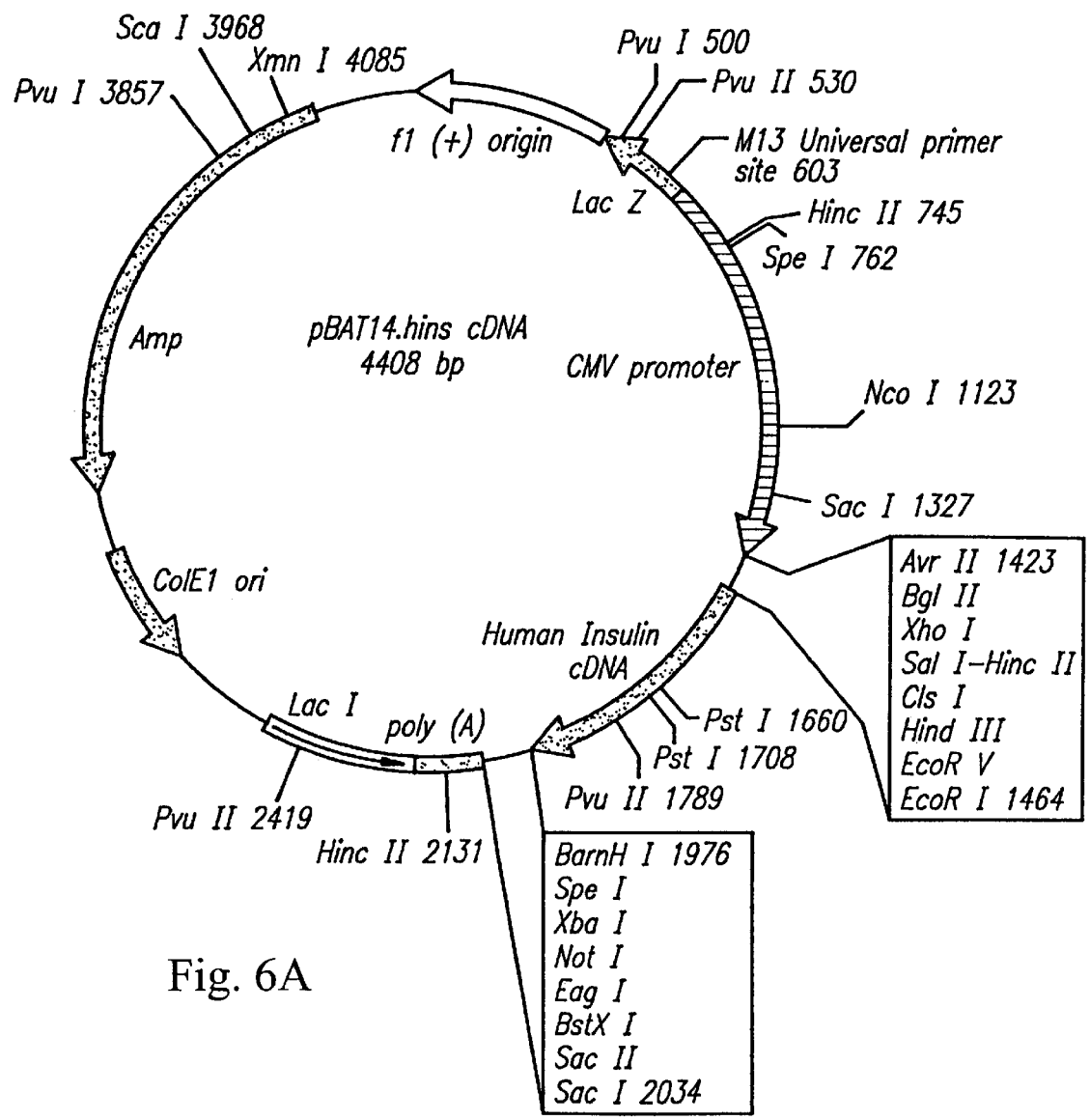
FIGS. 6A and 6B are maps of the pBAT14.hIns and pBAT16.hInsG1.M2 constructs, which contain a nucleotide sequence encoding human insulin or a mutant of human insulin, respectively, operably linked to a CMV promoter.
Figure 6B:
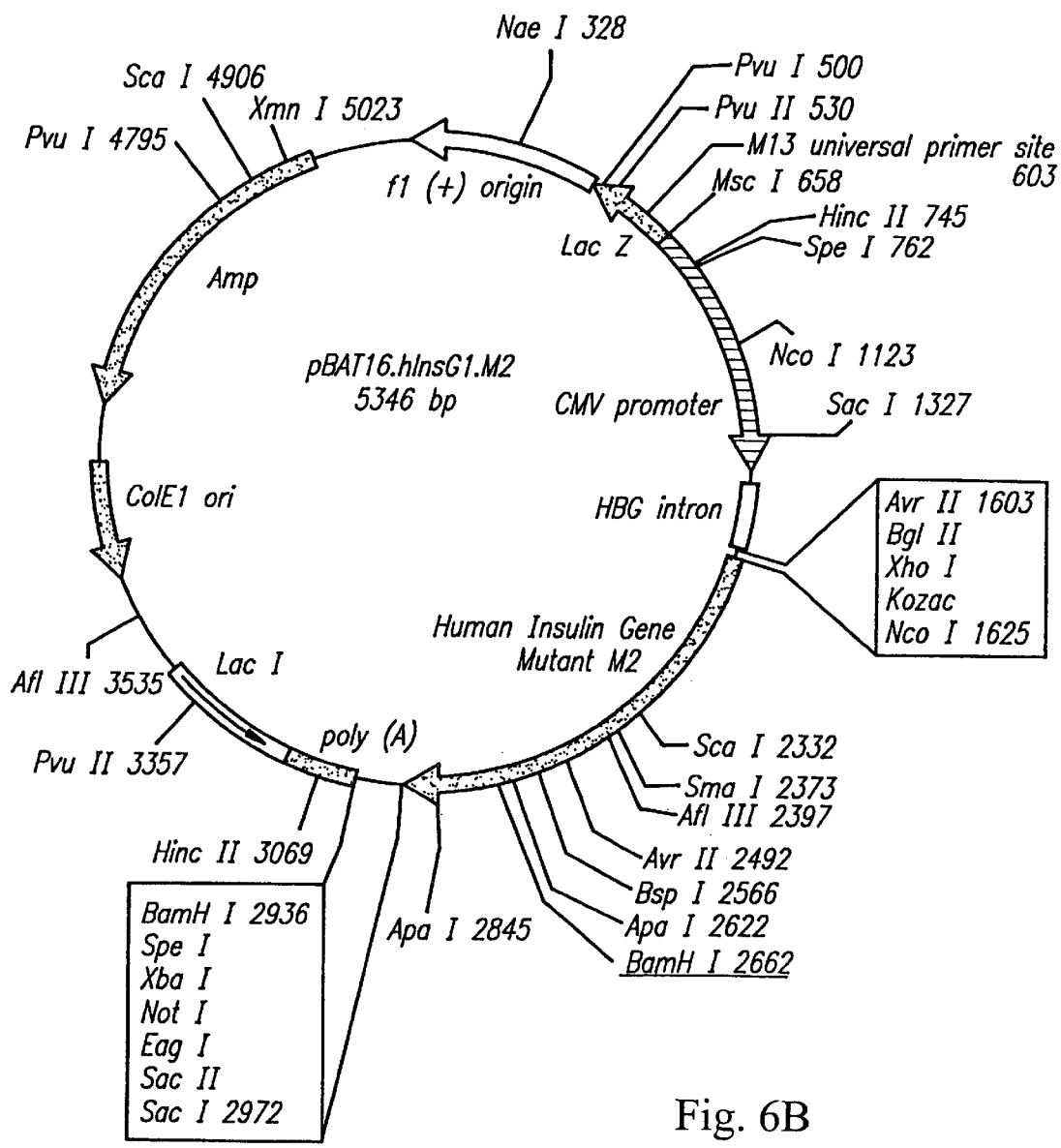

Example 3
Construction of Vectors Expressing Human Insulin (hIns) For Intestinal Cell Transformation Two constructs for expression of human insulin and a human insulin mutant were prepared using techniques well known in the art (see, for example, Sambrook et al., Ibid). The first construct, pBAT14.hins, contains a cDNA sequence encoding human insulin which is inserted in the commercially available vector pBLUESCRIPT SK+™ (Stratagene, La Jolla Calif.) (FIG. 6A). The human insulin encoding sequence is operably linked to a promoter from the immediate early gene of human CMV, which is positioned upstream of the first intron of human $\beta$-globin and of the human insulin-encoding cDNA sequence. The second construct, pBAT16.hInsG1.M2, was constructed by operably linking the CMV promoter upstream of a nucleotide sequence encoding a mutant of human insulin (FIG. 6B). The mutation in the human insulin mutant changes the second protease site between peptides C and A into a furin recognition site in order to allow proper processing in non-endocrine cells.

Example 4
In Vivo Gene Transfer of DNA Encoding Human Insulin by Introduction of Naked DNA Into the Intestinal Lumen Experimental diabetes was induced in rats by intravenous injection of 50 mg/kg of streptozotocin. Streptozotocin treatment produces high blood sugar levels within 24 hours after injection. Immediately after streptozotocin injection, the rat was anesthetized with pentobarbital and a laparotomy performed as described above. One ml of material (either PBS alone, PBS with the insulin vector pBAT16.hInsG1.M2 was instilled into the duodenum just below the pyloric junction in either streptozotocin treated or control animals. The material was primarily composed of naked DNA; no lipofectin, dendrimers, or other material to enhance introduction of the DNA into the cells was used. The abdomen was then closed with sutures. Control dye measurements showed that over a period of about an hour the material remains in great part in the upper portion of the duodenum. Recovery after surgery was nominal, and no signs or symptoms of disease were observed over the next 48 hours. At autopsy, the intestine looked normal in all respects.

Figure 7:
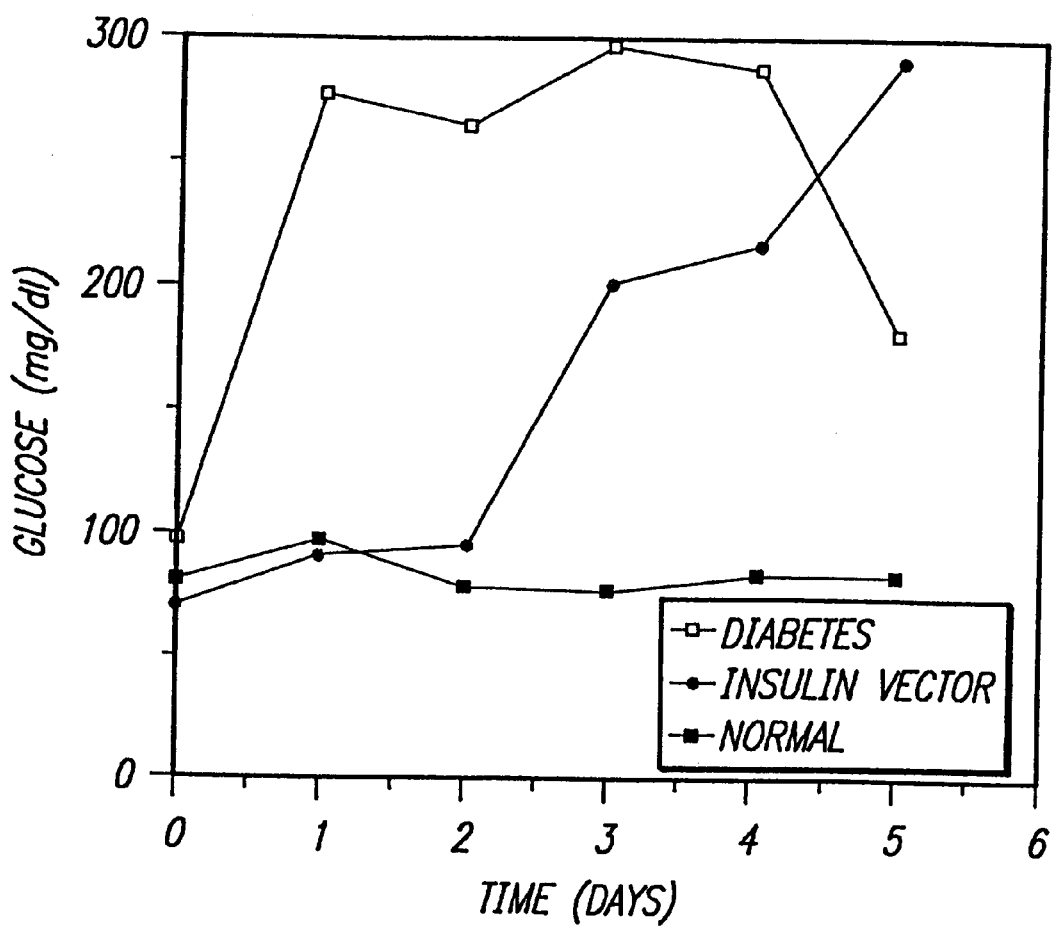
FIG. 7 is a graph showing amelioration of diabetes by intestinal cell transformation according to the invention. Open squares, blood glucose levels (mg/dl) in normal rats; open squares with center dot, blood glucose levels in rats having streptozotocin-induced diabetes; closed squares, blood glucose levels in rats having streptozotocin-induced diabetes and treated by intestinal cell transformation with an insulin-encoding vector.

Blood samples were obtained immediately prior to surgery and every 24 hours after treatment. The rat that received no treatment (no surgery or streptozotocin treatment) were used as negative controls to show the normal blood glucose level in untreated rats. Results are shown in FIG. 7. Streptozotocin-induced diabetes was ameliorated in the insulin vector-treated rats for at least 48 hours after treatment. Blood glucose levels in the insulin-vector treated rats were normal or near normal for at least 48 hours. These data show that the intestinal cells of the rats were successfully transformed with the human insulin-encoding vector, human insulin was both expressed and secreted into the blood stream, and that human insulin successfully suppressed the diabetic syndrome in the streptozotocin-treated rats. Furthermore, after the vector was no longer effective, diabetes re-emerged in the streptozotocin-treated rats.

Example 5
Efficiency of Intestinal Cell Transformation in Small and Large Intestine of Anesthetized Rats Rats are anesthetized with pentobarbital and various areas of the intestine exposed and isolated. Intestinal segments of approximately 5 cm in length are isolated and the plasmid formulation injected into the isolated segments for various periods of time in various volumes. Following administration, the abdomen is closed and the animal allowed to recover. Blood samples are then assessed for the presence of the gene product of the introduced DNA. In addition, the animals are sacrificed and transformed tissue extracted and assayed for expression of the introduced DNA.

Example 6
Efficiency of Intestinal Cell Transformation in Small and Large Intestine of Awake Rats A catheter is installed into the upper duodenum which exits the body in the rear of the neck. The plasmid formulation is instilled into the duodenum of awake rats via this catheter. The amount of DNA injected and the duration of administration are varied to assess the effect of these variables on transformation efficacy as measured by serum levels and tissue expression of the gene product of the introduced DNA as described in Example 5.

Figure 8:
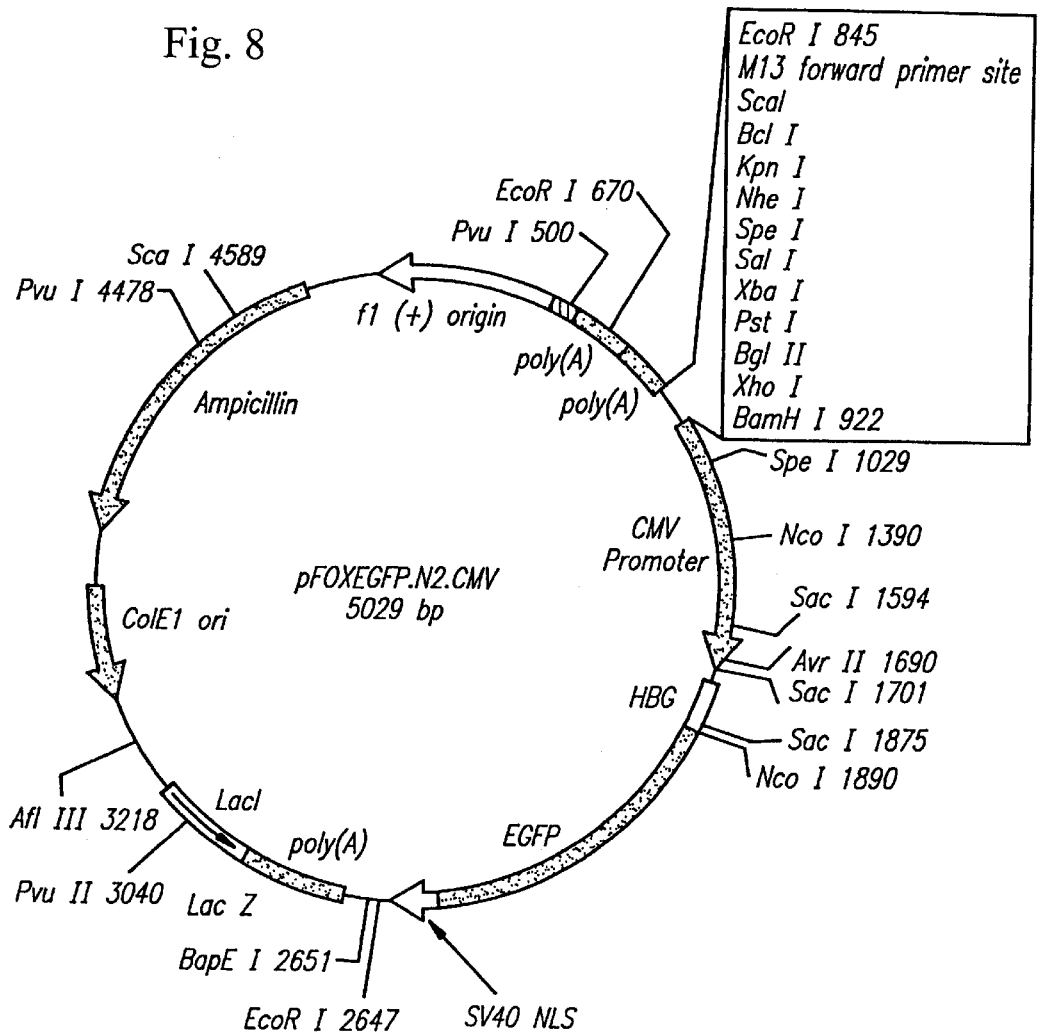
FIG. 8 is a map of the pFOXEGFP.N2.CMV construct, which encodes green fluorescent protein under control of a CMV promoter.

Example 7
Identification and Characterization of Transformed Intestinal Epithelial Cells Following Administration of Naked DNA The intestinal cell types transformed using the method of the invention, and expression of a protein encoded by the transforming construct is determined by examining expression of green fluorescent protein (GFP) in rat intestinal cells after in vivo administration of a construct encoding GFP. One ml of either PBS alone (negative control) or PBS with the GFP-encoding vector pFOXEGFP.N2.CMV (FIG. 8; see also German and Wang 1994 *Mol. Cell. Biol.* 14:4067) is instilled into the duodenum just below the pyloric junction in rats as described in Example 4. The abdomen is then closed with sutures. At 24 hours after treatment, tissue samples are obtained from the intestine of rats and fixed in 1.5% glutaraldehyde, and frozen sections prepared. Expression of GFP is detected in the sections using a fluorescent microscope and the number and types of cells expressing GFP are determined.

Example 8
Oral Gene Therapy in Humans Using Naked DNA

The DNA of interest is formulated as a capsule ("gene pill") according to methods well known in the art. The capsule comprises approximately 100 mg to 1000 mg of the DNA of interest. The capsule can additional contain liposomes, viral uptake elements, DNAase inhibitors, and/or various enteric coatings. Preferably, the capsule is primarily composed of naked DNA (i.e., DNA without viral uptake elements, dendrimers, lipofectin, or other compounds or agents that are used in conventional formulations to enhance cellular uptake) and can additionally contain components that provide for protection of the DNA against DNAses or degradation or damage that may occur while traversing the gastrointestinal tract to reach the desired intestinal cells.

The pill is administered to the human patient in order to achieve a sufficient level of expression of the protein encoded by the DNA within the pill. The pill can be administered, for example, several times daily, daily, or several times a week, depending upon the desired level of protein expression desired and/or the period over which therapy is desired. Therapy can be assessed by, for example, examining levels of protein present in the bloodstream of the patient (where the protein is secreted into the bloodstream), or by monitoring the patient for improvement or stabilization of his condition.

Example 9
Intestinal Cell Gene Therapy Using Naked DNA in a Suppository

The DNA of interest is formulated as a suppository according to methods well known in the art. The capsule comprises approximately 100 mg to 1000 mg of the DNA of interest. The capsule can additional contain liposomes, viral uptake elements, DNAase inhibitors, and/or various enteric coatings. Preferably, the suppository is primarily composed of naked DNA (i.e., DNA without viral uptake elements, dendrimers, lipofectin, or other compounds or agents that are used in conventional formulations to enhance cellular uptake) and can additionally contain components that provide for protection of the DNA against DNAses or degradation or damage that may occur while traversing the gastrointestinal tract to reach the desired intestinal cells.

The suppository is administered to the human patient in order to achieve a sufficient level of expression of the protein encoded by the DNA within the pill. The suppository can be administered, for example, several times daily, daily, or several times a week, depending upon the desired level of protein expression desired and/or the period over which therapy is desired. Therapy can be assessed by, for example, examining levels of protein present in the bloodstream of the patient (where the protein is secreted into the bloodstream), or by monitoring the patient for improvement or stabilization of his condition.

Following procedures similar to those described above, other therapeutic proteins can be expressed from DNA inserted in the genome of an intestinal epithelial cell by gene transfer according to the invention.

The invention now being fully described, it will be apparent to one of ordinary skill in the art that many changes and modifications can be made thereto without departing from the spirit or scope of the appended claims.

What is claimed is:

1. A method for reducing blood glucose levels in a hyperglycemic mammal, the method comprising:
    introducing a formulation directly into the gastrointestinal tract lumen of a hyperglycemic mammalian subject, the formulation comprising a DNA construct not packaged in a viral particle, wherein the construct encodes a functionally active insulin polypeptide that mediates reduction of blood glucose levels following introduction into the bloodstream, and wherein said DNA construct enters an intestinal epithelial cell and the encoded insulin polypeptide is expressed and delivered into the bloodstream of the mammal in an amount effective to reduce blood glucose levels.

2. The method of claim 1, wherein blood glucose levels are reduced for a period of at least about 24 hours.

3. The method of claim 1, wherein the functionally active insulin polypeptide is delivered to the bloodstream for a period of from about two to four days.

4. The method of claim 1, wherein blood glucose levels are within a normal range of blood glucose levels for a period of at least about 48 hours.

5. The method of claim 1, wherein the blood glucose levels are reduced to blood glucose levels within a normal range of blood glucose levels.

6. The method of claim 1, wherein the gastrointestinal cell is other than an intestinal stem cell.

7. The method of claim 1, wherein the gastrointestinal cell is within the small intestine.

8. The method of claim 1, wherein the gastrointestinal cell is a cell within the large intestine.

9. The method of claim 1, wherein said introducing is by oral administration.

10. A method of reducing blood glucose levels in a hyperglycemic mammal to a normal blood glucose level, the method comprising:

introducing a formulation directly into the gastrointestinal tract lumen of a hyperglycemic mammal, the formulation comprising a DNA construct not packaged in a viral particle, wherein the construct encodes a functionally active insulin polypeptide that mediates reduction of blood glucose levels following introduction into the bloodstream, and wherein said DNA construct enters an intestinal epithelial cell and the encoded insulin polypeptide is expressed and delivered into the bloodstream of the mammal in an amount effective to reduce blood glucose levels in the hyperglycemic mammal to a normal blood glucose level.

11. The method of claim 10, wherein blood glucose levels are reduced to a normal blood glucose level for a period of at least about 24 hours.

12. The method of claim 10, wherein blood glucose levels are within a normal range of blood glucose levels for a period of at least about 48 hours.

13. The method of claim 9, wherein the functionally active insulin polypeptide is delivered to the bloodstream for a period of from about two to four days.

14. The method of claim 10, wherein said introducing is by oral administration.

* * * * *

UNITED STATES PATENT AND TRADEMARK OFFICE
CERTIFICATE OF CORRECTION

PATENT NO. : 6,225,290 B1
DATED : May 1, 2001
INVENTOR(S) : Michael German, Ira D. Goldfine, Stephen S. Rothman It is certified that error appears in the above-identified patent and that said Letters Patent is hereby corrected as shown below:

<u>Title page,</u>
Item [22], delete and insert therefor -- Item [22], Field: Sep. 20, 1996 --

Signed and Sealed this

Twenty-third Day of April, 2002

Attest:

Attesting Officer

JAMES E. ROGAN
*Director of the United States Patent and Trademark Office*